US006274585B1

(12) United States Patent
Cui et al.

(10) Patent No.: US 6,274,585 B1
(45) Date of Patent: Aug. 14, 2001

(54) DIHYDROPYRIMIDINES AND USES THEREOF

(75) Inventors: Donghui Cui, Newtown, PA (US); Margaret R. Davis, Redmond, WA (US); Michael Dunn, Cambridge, MA (US); Ben E. Evans, Lansdale; Hanumath P. Kari, Hatfield, both of PA (US); Bharat Lagu, Maywood, NJ (US); Dhanapalan Nagarathnam, Bethany, CT (US); Kamlesh P. Vyas, North Wales, PA (US); Kanyin Zhang, San Diego, CA (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/470,691

(22) Filed: Dec. 23, 1999

Related U.S. Application Data

(60) Provisional application No. 60/133,612, filed on Dec. 23, 1998.

(51) Int. Cl.$^7$ ..................... A61K 31/513; A61K 31/519; C07D 239/20; C07D 491/048
(52) U.S. Cl. ...................... 514/258; 514/275; 544/278; 544/316
(58) Field of Search ................... 514/274, 278; 544/316, 258

(56) References Cited

U.S. PATENT DOCUMENTS

| 4,438,117 | 3/1984 | Cherkofsky | 424/251 |
|---|---|---|---|
| 4,684,653 | 8/1987 | Taylor et al. | 514/274 |
| 4,684,655 | 8/1987 | Atwal | 514/274 |
| 4,684,656 | 8/1987 | Atwal | 514/258 |
| 4,703,120 | 10/1987 | Press | 544/278 |
| 4,728,652 | 3/1988 | Atwal | 514/274 |
| 4,845,216 | 7/1989 | Taylor et al. | 544/279 |
| 4,855,301 | 8/1989 | Atwal et al. | 514/269 |
| 4,882,334 | 11/1989 | Shih et al. | 514/258 |
| 4,902,796 | 2/1990 | Taylor et al. | 544/279 |
| 4,946,846 | 8/1990 | Nomura et al. | 514/258 |
| 5,134,145 | 7/1992 | Brouwer et al. | 514/274 |
| 5,149,810 | 9/1992 | Perrior et al. | 544/309 |
| 5,202,330 | 4/1993 | Atwal | 514/274 |
| 5,250,531 | 10/1993 | Cooper | 514/256 |
| 5,292,740 | 3/1994 | Burri et al. | 514/256 |
| 5,500,424 | 3/1996 | Nagamine et al. | 514/235.5 |
| 5,521,189 | 5/1996 | Boykin et al. | 514/256 |
| 5,541,186 | 7/1996 | Breu et al. | 514/256 |
| 5,594,141 | 1/1997 | Yuan et al. | 544/242 |
| 5,942,517 | * 8/1999 | Nagarathnam et al. | 514/274 |

FOREIGN PATENT DOCUMENTS

| 0162208 | 11/1985 | (EP) . |
|---|---|---|
| 0204317 | 12/1986 | (EP) . |
| 0234830 | 9/1987 | (EP) . |
| 0236902 | 9/1987 | (EP) . |
| 0237347 | 9/1987 | (EP) . |
| 0280227 | 8/1988 | (EP) . |
| 0400665 | 12/1990 | (EP) . |
| 0459666 | 12/1991 | (EP) . |
| 0622366 | 11/1994 | (EP) . |
| 0622369 | 11/1994 | (EP) . |
| 0627427 | 12/1994 | (EP) . |
| 2610625 | 8/1988 | (FR) . |
| 61-282367 | 12/1986 | (JP) . |
| 62-87574 | 4/1987 | (JP) . |
| 62-265271 | 11/1987 | (JP) . |
| 9200741 | 1/1992 | (WO) . |
| 9214453 | 9/1992 | (WO) . |
| 9410989 | 5/1994 | (WO) . |
| 9422829 | 10/1994 | (WO) . |
| WO 96/14846 | * 5/1996 | (WO) . |
| WO 97/42956 | * 11/1997 | (WO) . |
| WO 98/51311 | * 11/1998 | (WO) . |
| WO 99/07695 | * 2/1999 | (WO) . |
| WO 99/48530 | * 9/1999 | (WO) . |

OTHER PUBLICATIONS

Atwal, K.S. et al., "Dihydropyrimidine Calcium Channel Blockers. 3. 3–Carbamoyl–4–aryl–1,2,3, 4–tetrahydro–6–methyl–pyrimidenecarboxylic Acid Esters as Orally Effective Antihypertensive Agents," *Journal of Medicinal Chemistry*, (1991) 34(2): 76–81.

Cho H., Takeuchi Y., Ueda M., and Mizuno A., Regioselective synthesis of N–substituted dihydropyrimidine–2 (1–H) or (3H)—One., *Tetrahedron Letters*, (1988) vol. 29(42): 5405–5408.

Atwal, K.S. et al., "Synthesis of Substituted 1,2,3,4–Tetrahydro–6–Methyl–2–Thioxo–5–Pyrimidinecarboxylic Acid Esters," *Heterocycles* (1987) 26(5): 1189–1192 (Exhibit 39).

Atwal, K.S. et al., "Substituted 1,4–Dihydropyrimidines. 3. Synthesis of Selectively Functionalized 2–Hetero–1,4–dihydropyimidines," *Journal of Organic Chemistry* (1989) 54: 5898–5907 (Exhibit 40).

Atwal, K.S. et al., "Dihydropyrimidine Calcium Channel Blockers: 2–Heterosubstituted 4–aryl–1, 4–dihydro–6–methyl–5–pyrimidinecarboxylic Acid Esters as Potent Mimics of Dihydropyridines," *Journal of Medicinal Chemistry* (1990) 33(5): 1510–1515 (Exhibit 41).

(List continued on next page.)

Primary Examiner—Richard L. Raymond
(74) Attorney, Agent, or Firm—John P. White; Cooper & Dunham LLP

(57) ABSTRACT

This invention is directed to dihydropyrimidines which are selective antagonists for human $\alpha_{1a}$ receptors. This invention is also related to uses of these compounds for relaxing lower urinary tract tissue, treating benign prostatic hyperplasia and for the treatment of any disease where the antagonism of the $\alpha_{1a}$ receptor may be useful. The invention further provides a pharmaceutical composition comprising a therapeutically effective amount of the above-defined compounds and a pharmaceutically acceptable carrier.

29 Claims, 3 Drawing Sheets

OTHER PUBLICATIONS

Atwal, K.S. et al., "Dihydropyrimidine Calcium Channel Blockers. 2. 3–Substituted–4–aryl–1,4–dihydro–6–methyl–5–pyrimidinecarbosylic Acid Esters as Potent Mimics of Dihydropyridines," *Journal of Medicinal Chemistry* (1990) 33(9): 2629–2635 (Exhibit 42).

Atwal, K.S. et al., "Dihydropyrimidine Calcium Channel Blockers. 3. 3–Carbamoyl–4–aryl–1,2,3,4–tetrahydro–6–methyl–5–pyrimidenecarboxylic Acid Esters as Orally Effective Antihypertensive Agents," *Journal of Medicinal Chemistry* (1991) 34(2): 806–811 (Exhibit 43).

Barrio, et al., "A Direct Method For Preparation of 2–Hydroxyethoymethyl Derivatives of Guanine, Adenine, and Cytosine," *Journal of Medicinal Chemistry* (1980) 23(5): 572–574 (Exhibit 44).

Brown, et al., "Inhibitors of *Bacillus subtilis* DNA Polymerase III. 6–(Arylalkylamino)uracils and 6–Anilinouracils," *Journal of Medicinal Chemistry* (1977) 20(9): 1186–1189 (Exhibit 46).

Cho, H. et al., "Dihydropyrimidines: Novel Calcium Antagonists with Potent and Long–Lasting Vasodilative and Antihypertensive Activity," *Jorunal of Medicinal Chemistry* (1989) 32: 2399–2406 (Exhibit 47).

Khanina, E.L. et al., Alkylation of derivatives of 2–oxo–4–phenyl–6–methyl–1,2,3,4–tetrahydropyrimidine–5–carboxlic acid. Chemical Abstracts 89: 43319 (1978) (Exhibit 50).

Mamaev, V.P. amd Dubovenko, Z.D., Phyrimidines. XXI. 5–Substituted 2–hydroxy–4,6–diphenylpyrimidines. Chemical Abstracts 73: 77187 (1970) (Exhibit 51).

Rovnyak, G.C. et al., "Dihydropyrimidine Calcium Channel Blockers. 4. Basic 3–Substituted–4–aryl–1,4–dihydropyrimidine–5–carboxylic Acid Esters," *Journal of Medicinal Chemistry* (1992) 35(17): 3254–3263 (Exhibit 53).

Wetzel, J.M., et al., "Discovery of $\alpha_{1a}$–Adrenergic Receptor Antagonists Based on the L–Type $Ca^{2+}$ Channel Antagonist Niguldipine" *Journal of Medicinal Chemistry* (1995) 38(10): 1579–1581 (Exhibit 56).

* cited by examiner

Compound 5

Compound 6

Compound 7

Compound 8

Compound 9

DIHYDROPYRIMIDINES AND USES THEREOF

This application claims the benefit of U.S. Provisional Application No. 60/133,612, filed Dec. 23, 1998, the contents of which are hereby incorporated in their entirety by reference into the present application.

Throughout this application, various references are referred to within parentheses. Disclosures of these publications in their entireties are hereby incorporated by reference into this application to more fully describe the state of the art to which this invention pertains.

BACKGROUND OF THE INVENTION

The designation "$\alpha_{1A}$" is the appellation recently approved by the IUPHAR Nomenclature Committee for the previously designated "$\alpha_{1C}$" cloned subtype as outlined in the 1995 Receptor and Ion Channel Nomenclature Supplement (Watson and Girdlestone, 1995). The designation $\alpha_{1A}$ is used throughout this application and the supporting tables and figures to refer to this receptor subtype. At the same time, the receptor formerly designated $\alpha_{1A}$ was renamed $\alpha_{1D}$. The new nomenclature is used throughout this application. Stable cell lines expressing these receptors are described herein; however, these cell lines were deposited with the American Type Culture Collection (ATCC) under the old nomenclature (infra).

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors (McGrath, et. al. *Med. Res. Rev.*, 9, 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors ($\alpha_1$ and $\alpha_2$) existed in the central and peripheral nervous systems. Since 1988, new techniques in molecular biology have led to the identification of at least six α-adrenergic receptors which exist throughout the central and peripheral nervous systems: $\alpha_{1A}$ (new nomenclature), $\alpha_{1B}$, $\alpha_{1D}$ (new nomenclature), $\alpha_{2A}$, $\alpha_{2B}$ and $\alpha_{2C}$ (Bylund, D. B., FASEB J., 6, 832 (1992)). In many cases, it is not known precisely which physiological responses in the body are controlled by each of these receptors. In addition, current α-adrenergic drugs are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects such as dizziness and asthenia which severely limit its use in treating patients on a chronic basis. More recently, the α-adrenergic antagonists prazosin and terazosin have also been found to be useful for treating BPH.

However, these drugs also produce untoward side effects. It has recently been discovered that the $\alpha_{1A}$ receptor is responsible for mediating the contraction of human prostate smooth muscle (Gluchowski, C. et. al., WO 94/10989, 1994; Forray, C. et. al., *Mol. Pharmacol.* 45, 703, 1994). This discovery indicates that the $\alpha_{1A}$ antagonists may be effective agents for the treatment of BPH with decreased side effects. Further studies have indicated that the $\alpha_{1A}$ receptor may also be present in other lower urinary tract tissues, such as urethral smooth muscle (Ford et al. Br. J. Pharmacol., 114, 24P, (1995)).

This invention is directed to dihydropyrimidine compounds which are selective antagonists for cloned human $\alpha_{1A}$ receptors. This invention is also related to uses of these compounds for treating benign prostatic hyperplasia, and for the treatment of any disease where antagonism of the $\alpha_{1A}$ receptor may be useful.

SUMMARY OF THE INVENTION

This invention is directed to compounds having the structure:

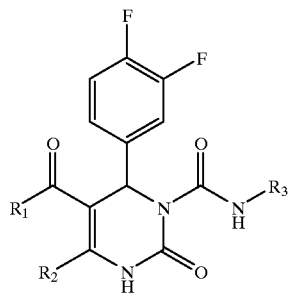

wherein R₁ is —OCH₃ or OH;
wherein R₂ is —CH₂OH, —CH₂OCH₃, or —COOH;
wherein R₁ and R₂ together form a 5-membered lactone ring;
wherein R₃ is selected from the group consisting of —(CH₂)₃OH,

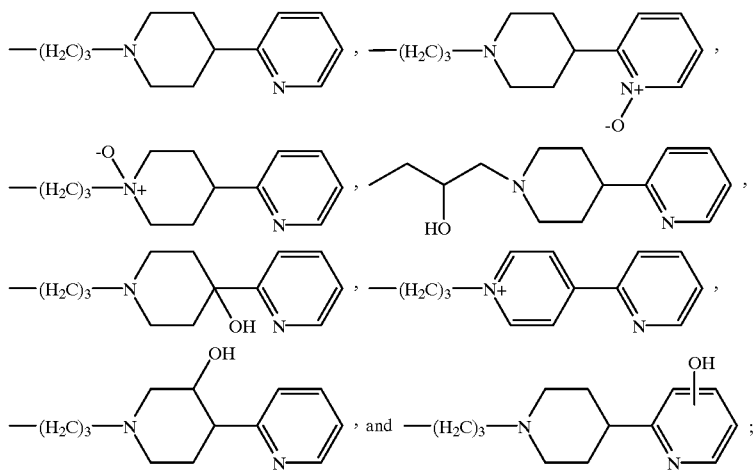

provided that when R₁ is OH, R₃ cannot be

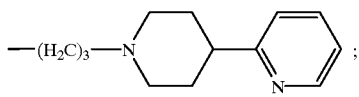

or a pharmaceutically acceptable salt thereof.

This invention is also directed to a compound having the structure:

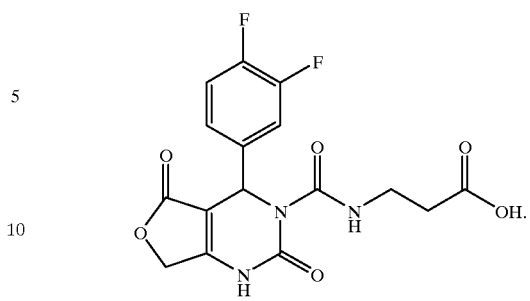

This invention provides a pharmaceutical composition comprising a therapeutically effective amount of any one of the compounds described herein and a pharmaceutically acceptable carrier.

This invention also provides a method of treating a subject suffering from benign prostatic hyperplasia which comprises administering to the subject an amount of any one of the compounds described herein effective to treat benign prostatic hyperplasia.

This invention provides a method of relaxing lower urinary tract tissue which comprises contacting the lower urinary tract tissue with an amount of any one of the compounds described herein effective to relax lower urinary tract tissue.

This invention provides a method of inhibiting contraction of prostatic tissue in a subject which comprises administering an amount of any one of the compounds described herein effective to inhibit contraction of prostatic tissue.

This invention provides a method of treating a disease which is susceptible to treatment by antagonism of the α$_{1A}$ receptor which comprises administering to the subject an amount of any one of the compounds described herein effective to treat the disease.

This invention provides a pharmaceutical composition comprising a therapeutically effective amount of any one of the compounds described herein in combination with a therapeutically effective amount of finasteride and a pharmaceutically acceptable carrier.

This invention provides a process of making a pharmaceutical composition comprising combining a therapeutically effective amount of any one of the compounds described herein and a pharmaceutically acceptable carrier.

BRIEF DESCRIPTION OF THE FIGURES

FIGS. 1A–1C show the structures of Compounds 1 to 9, described herein in the Examples.

DETAILED DESCRIPTION OF THE INVENTION

Figure 1A:
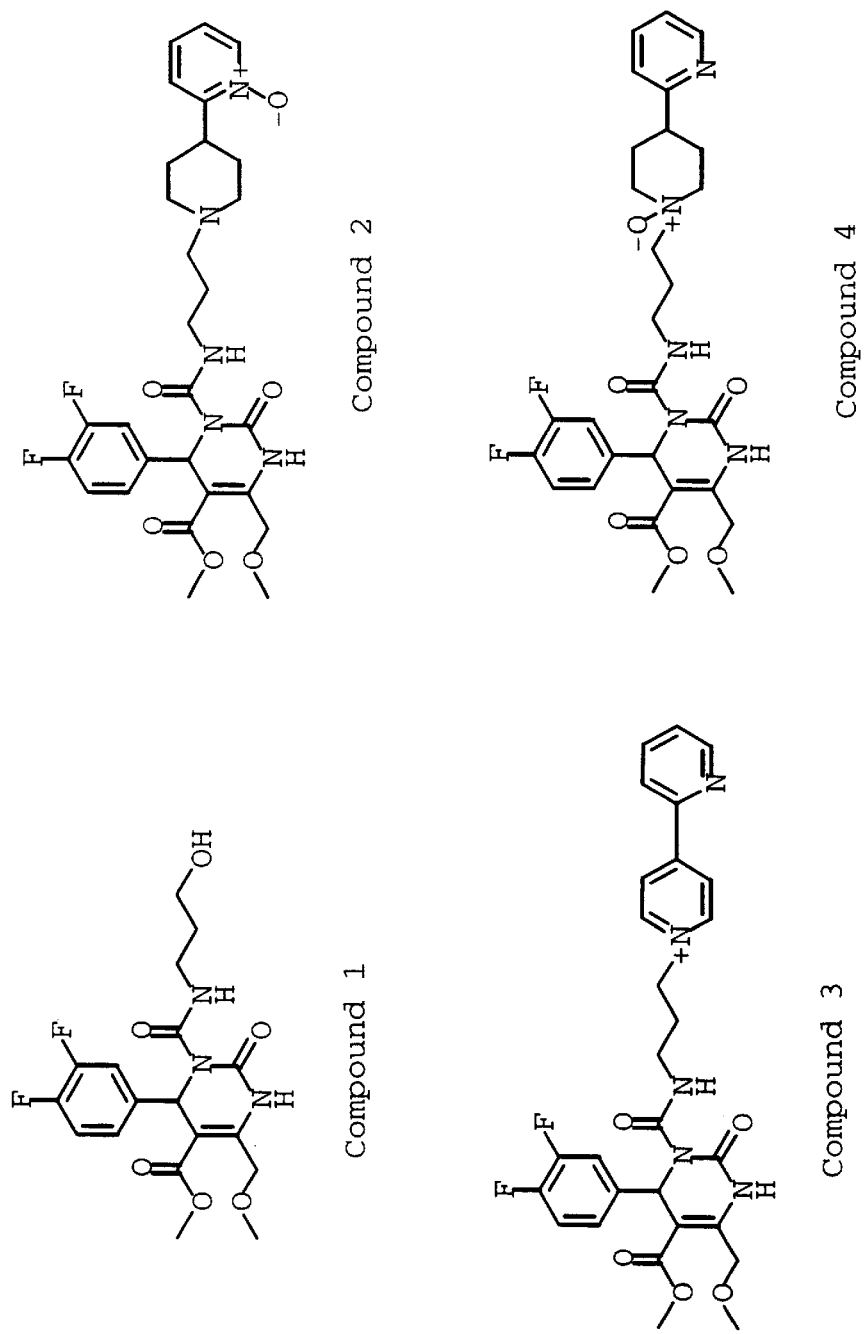
FIGS. 1A–1C.
Figure 1B:
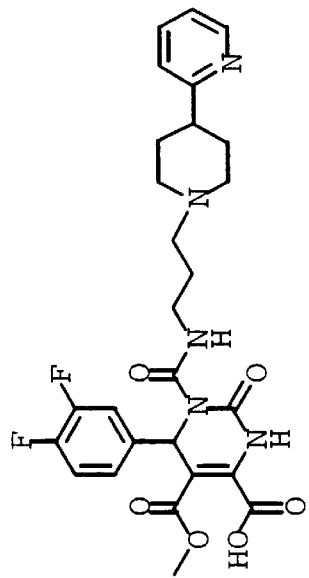
Figure 1B:
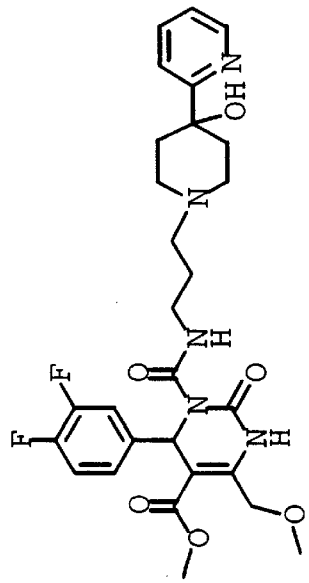
Figure 1B:
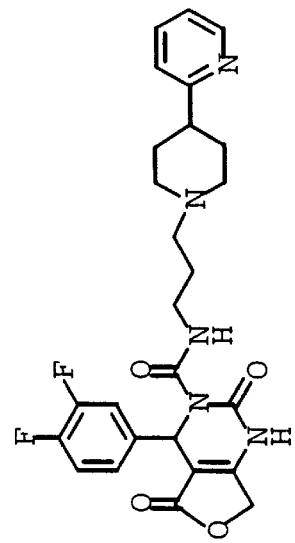
Figure 1B:
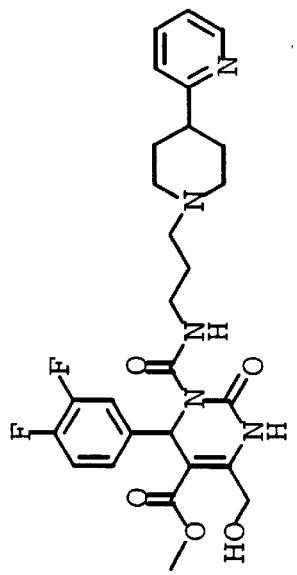
Figure 1C:
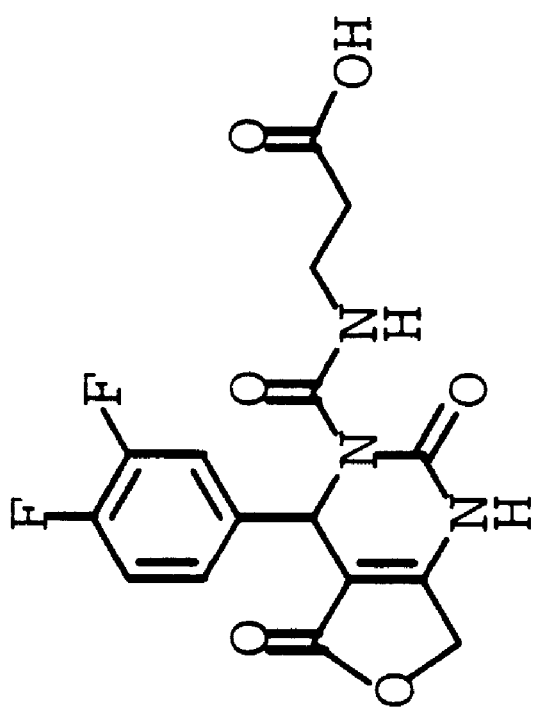

The present invention is directed to compounds having the following structure:

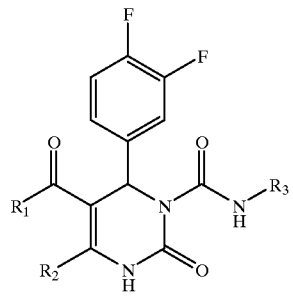

wherein $R_1$ is —OCH$_3$ or OH;
wherein $R_2$ is —CH$_2$OH, —CH$_2$OCH$_3$, or —COOH;
wherein $R_1$ and $R_2$ together form a 5-membered lactone ring;
wherein $R_3$ is selected from the group consisting of —(CH$_2$)$_3$OH,

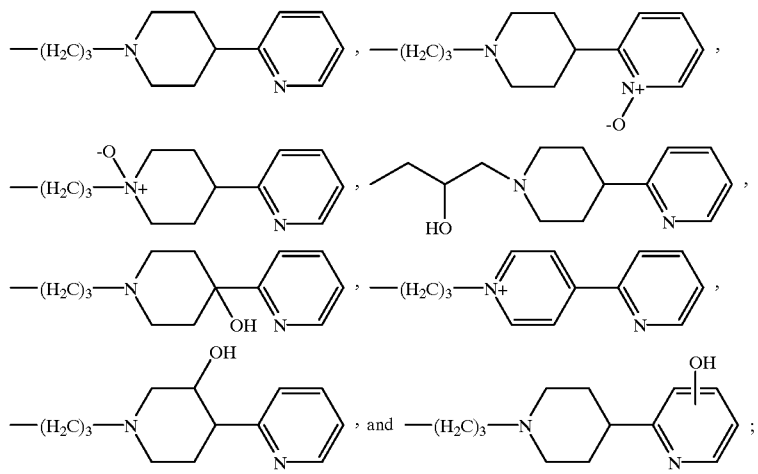

provided that when $R_1$ is OH, $R_3$ cannot be

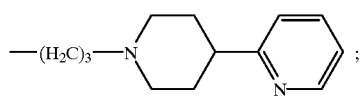

or a pharmaceutically acceptable salt thereof.

The present invention also provides for the (+) and (−) enantiomers of all of the compounds described herein.

The invention further provides for the cis and trans isomers of all of the compounds described herein. It is noted that the terms "cis" and "trans" correspond to relative stereochemistry, as determined, for example by NOE (Nuclear Overhauser Effect) experiments.

The compounds of the present invention may be present as enantiomers, diasteriomers, isomers or two or more of the compounds may be present to form a racemic mixture. Furthermore, the compounds of the present invention are preferably at least 80% pure, more preferably 90% pure, and most preferably 95% pure.

In one embodiment the compound has the following structure:

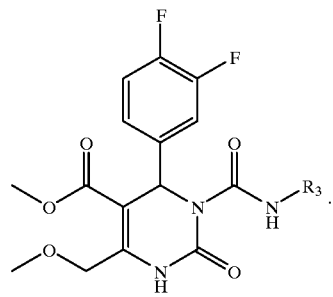

In another embodiment of the present invention the compound is:

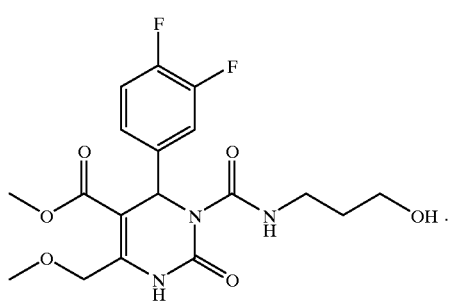

In a further embodiment of the present invention the compound is:

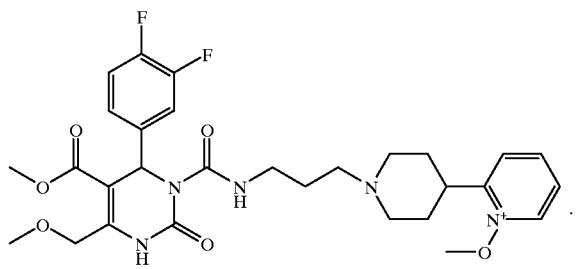

In yet a further embodiment of the present invention the compound is:

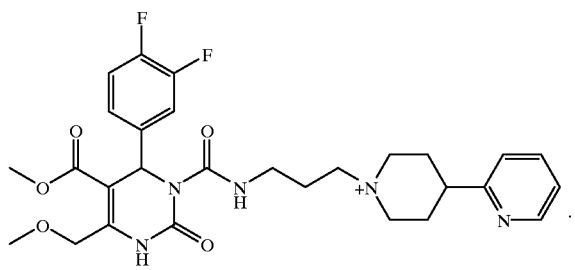

In an embodiment of the present invention the compound is:

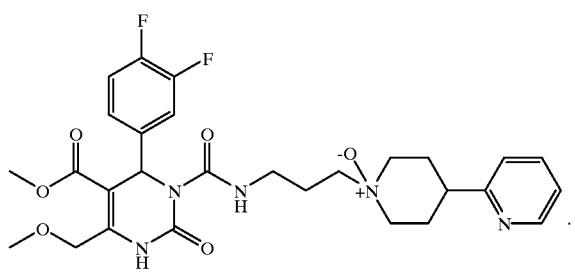

In an embodiment of the present invention, R₃ is selected from the group consisting of

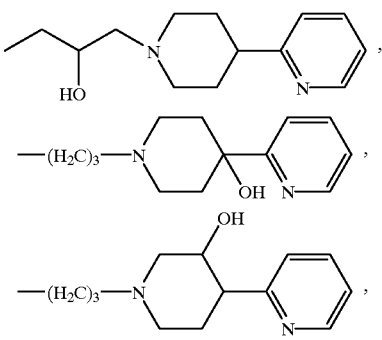

and

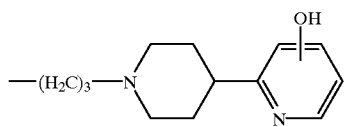

In a further embodiment of the present invention the compound has the following structure:

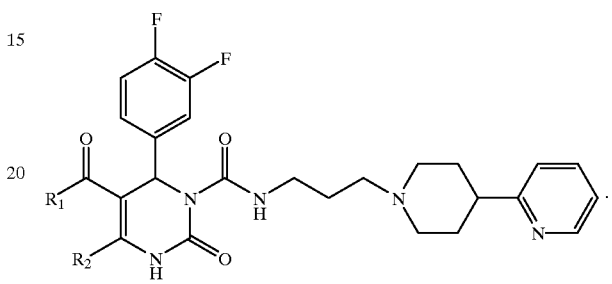

In an embodiment of the present invention the compound is:

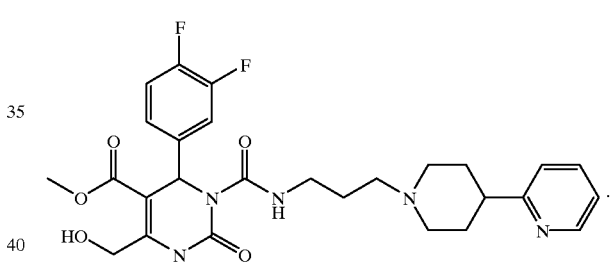

In yet another embodiment of the present invention the compound is:

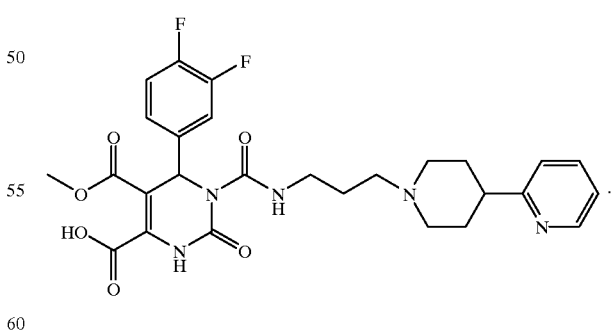

In yet another embodiment of the present invention the compound is:

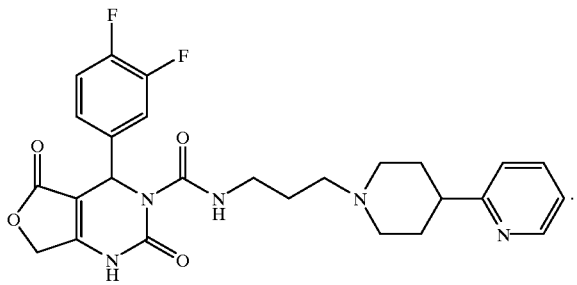

The present invention also provides a compound having the structure:

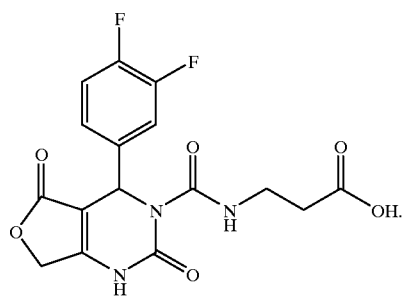

The invention also provides a pharmaceutical composition comprising a therapeutically effective amount of any of the compounds described herein and a pharmaceutically acceptable carrier. In the subject invention, a "therapeutically effective amount" is any amount of a compound which, when administered to a subject suffering from a disease against which the compounds are effective, causes reduction, remission, or regression of the disease.

In one embodiment, the therapeutically effective amount is an amount from about 0.01 mg per subject per day to about 500 mg per subject per day, preferably from about 0.1 mg per subject per day to about 60 mg per subject per day, more preferably from about 1 mg per subject per day to about 30 mg per subject per day.

In the practice of this invention, the "pharmaceutically acceptable carrier" is any physiological carrier known to those of ordinary skill in the art useful in formulating pharmaceutical compositions.

In one embodiment the pharmaceutical carrier may be a liquid and the pharmaceutical composition would be in the form of a solution. In another embodiment, the pharmaceutically acceptable carrier is a solid and the composition is in the form of a tablet or powder. In a further embodiment, the pharmaceutical carrier is a gel and the composition is in the form of a suppository or a cream. In yet a further embodiment, the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In a further embodiment of the present invention, any one of the compounds described herein additionally does not cause a fall in blood pressure at dosages effective to alleviate benign prostatic hyperplasia.

This invention provides a method of treating a subject suffering from benign prostatic hyperplasia (BPH) which comprises administering to the subject any one of the compounds described herein effective to treat BPH. The invention further provides that the compound additionally does not cause a fall in blood pressure at dosages effective to alleviate BPH. In one preferred embodiment the compound effects treatment of BPH by relaxing lower urinary tract tissue and in particular where the lower urinary tract tissue is urethral smooth muscle.

In the practice of this invention, the term "lower urinary tract tissue" is used to include prostatic capsule, prostate urethra, bladderneck, urethral smooth muscle and prostatic smooth muscle.

This invention also provides a method of treating a subject suffering from benign prostatic hyperplasia, which comprises administering to the subject one of the compounds described herein in combination with a 5-alpha reductase inhibitor effective to treat benign prostatic hyperplasia. In one embodiment the 5-alpha reductase inhibitor is finasteride.

This invention further provides a method of relaxing lower urinary tract tissue which comprises contacting the lower urinary tract tissue with an amount of one of the compounds described herein effective to relax lower urinary tract tissue. In one embodiment the lower urinary tract tissue is urethral smooth muscle. In one preferred embodiment the compound additionally does not cause a fall in blood pressure when it is effective to relax lower urinary tract tissue.

The invention further provides for a method of inhibiting contraction of prostatic tissue, which comprises administering to the subject an amount of any of the compounds described herein effective to inhibit contraction of prostatic tissue. In one preferred embodiment the prostatic tissue is prostatic smooth muscle and the compound additionally does not cause a fall in blood pressure.

This invention also provides a method of treating a disease which is susceptible to treatment by antagonism of the $\alpha_{1A}$ receptor which comprises administering to the subject one of the compounds describe herein effective to treat the disease.

The invention provides a pharmaceutical composition comprising a therapeutically effective amount of any one of the compounds described herein in combination with a therapeutically effective amount of finasteride and a pharmaceutically acceptable carrier. This invention also provides for a pharmaceutical composition comprising any one of the compounds described herein present in an amount from about 0.01 mg to about 500 mg and the therapeutically effective amount of the finasteride is about 5 mg. In one embodiment, the therapeutically effective amount of the compound is an amount from about 0.1 mg to about 60 mg and the therapeutically effective amount of the finasteride is about 5 mg. In another embodiment, the therapeutically effective amount of the compound is an amount from about 1 mg to about 30 mg and the therapeutically effective amount of the finasteride is about 5 mg.

This invention provides a pharmaceutical composition made by combining a therapeutically effective amount of any of the compounds described herein and a pharmaceutically acceptable carrier.

This invention also provides a pharmaceutical composition made by combining a therapeutically effective amount of any of the compounds described herein with a therapeutically acceptable amount of finasteride and a pharmaceutically acceptable carrier.

Included in this invention are pharmaceutically acceptable salts and complexes of all of the compounds described herein. The salts include, but are not limited to, the following acids and bases: Inorganic acids which include hydrochloric acid, hydrofluoric acid, hydrobromic acid, hydroiodic acid, sulfuric acid, and boric acid; organic acids which include acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid, and mandelic acid; inorganic bases include ammonia and hydrazine; and organic bases which include methylamine, ethylamine, hydroxyethylamine, propylamine, dimethylamine, diethylamine, trimethylamine, triethylamine, ethylenediamine, hydroethylamine, morpholine, piperazine, and guanidine. This invention further provides for the hydrates and polymorphs of all of the compounds described herein.

The present invention includes within its scope prodrugs of the compounds of this inventions. In general, such prodrugs will be functional derivatives of the compounds of the invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

One skilled in the art will readily appreciate that appropriate biological assays will be used to determine the therapeutic potential of the claimed compounds for treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Synthesis of Compounds 1–9

A. Synthesis of Compound 1

(+)-1,2,3,6-Tetrahydro-1-(3-hydroxypropyl) carboxamido-5-methoxycarbonyl-4-methoxymethyl-6-(3,4-difluorophenyl)-2-oxo-pyrimidine a) 5-Methoxycarbonyl-4-methoxymethyl-1,2,3,6-tetrahydro-2-oxo-6-(3,4-difluorophenyl)-pyrimidine To a well-stirred mixture of methyl 4-methoxyacetoacetate (50 g, 0.351 mol), 3,4-difluorobenzaldehyde (51.39 g, 0.351 mmol), and urea (31.64 g, 0.527 mole) in THF (300 mL) at room temperature were added copper(I) oxide (5.06 g, 0.035 mole) and acetic acid (2.05 mL) sequentially followed by dropwise addition of boron trifluoride diethyl etherate (56 mL, 0.456 mole). The mixture was stirred and refluxed for 8 h, whereupon TLC (1/1 EtOAc/hexanes) indicated completion of the reaction. It was cooled and poured into a mixture of ice and sodium bicarbonate (100 g) and the resulting mixture was filtered through Celite. The Celite pad was washed with dichloromethane (400 mL). The organic layer was separated from the filtrate and the aqueous layer was extracted with more dichloromethane (3×300 mL). The combined organic extracts were dried (sodium sulfate) and the solvent evaporated. The crude product was purified by flash column on silica gel using 50% ethyl acetate in hexanes and then ethyl acetate as eluents to give the product as a pale yellow foam, which on trituration with hexane became white powder (103.3 g, 94%). $^1$H NMR (CDCl$_3$) δ 3.476 (s, 3H), 3.651 (s, 3H), 4.653 (s, 2H), 5.39 (s, 1H), 6.60 (br s, 1H, NH), 7.00–7.20 (m, 3H), 7.72 (br s, 1H, NH).

b) (+)-5-Methoxycarbonyl-4-methoxymethyl-1,2,3, 6-tetrahydro-2-oxo-6-(3,4-difluorophenyl)-pyrimidine The racemic intermediate 5-methoxycarbonyl-4-methoxymethyl-1,2,3,6-tetrahydro-2-oxo-6-(3,4-difluorophenyl)-pyrimidine was resolved by chiral HPLC [Chiralcel OD 20×250 mm #369-703-30604; 1 254 nm; hexanes/ethanol 90/10; 85 mg per injection; retention time of the desired enantiomer: 16.94 min., the first enantiomer peak to elute] to give (+)-5-methoxycarbonyl-4-methoxymethyl-1,2,3,6-tetrahydro-2-oxo-6-(3,4-difluorophenyl)-pyrimidine (40–42 wt % isolation of the desired enantiomer from the racemate); [α]$_D$=+83.8 (c=0.5, chloroform).

c) (+)-5-Methoxycarbonyl-4-methoxymethyl-1,2,3, 6-tetrahydro-2-oxo-6-(3,4-difluorophenyl)-1-[(4-nitrophenyloxy)-carbonyl]pyrimidine To a solution of (+)-5-methoxycarbonyl-4-methoxymethyl-1,2,3,6-tetrahydro-2-oxo-6-(3,4-difluorophenyl)-pyrimidine (1.98 g, 6.34 mmol) in anhydrous THF (20 mL) at −78° C. under argon atmosphere, a solution of lithium hexamethyldisilazide in THF (1M, 18 mL, 18 mmol) was added over 2–3 min. and the mixture was stirred for 10 min. This solution was added over 6 min. via a cannula to a stirred solution of 4-nitrophenyl chloroformate (4.47 g, 22.2 mmol) in THF (20 mL) at −78° C. The stirring was continued for 10 min and the mixture was poured onto ice (50 g) and extracted with chloroform (2×50 mL). The combined extracts were dried (sodium sulfate) and the solvent evaporated. The residue was purified by flash column chromatography using hexanes/ethyl acetate (4:1 to 3.5:1) as eluent. The product was obtained as a yellow syrup which on trituration with hexane became white powder (2.4 g, 79%). $^1$H NMR (CDCl$_3$) δ 3.522 (s, 3H), 3.744 (s, 3H), 4.65–4.80 (q, J=16.5 Hz, 2H), 6.323 (s, 1H), 7.10–7.30 (m, 4H), 7.358 (d, J=9 Hz, 2H), 8.273 (d, J=9 Hz, 2H).

d) (+)-1,2,3,6-Tetrahydro-1-(3-hydroxypropyl) carboxamido-5-methoxycarbonyl-4-methoxymethyl-6-(3,4-difluorophenyl)-2-oxo-pyrimidine To a solution of (+)-1,2,3,6-tetrahydro-6-(3,4-difluorophenyl)-5-methoxycarbonyl-4-methoxymethyl-1-[N-(4-nitrophenoxy)carbonyl]-2-oxopyrimidine(100 mg, 0.209 mmol) in dichloromethane (5 mL), 3-aminopropanol (0.2 mL, 2.62 mmol) was added at r.t. The resulting mixture was stirred for 2 hour and the crude product was purified through column chromatography on silica gel using EtOAc as the eluent (82 mg, 95%). $^1$H-NMR (300 MHZ, CDCl$_3$) δ 1.67–1.75 (m, 2H), 3.41–3.49 (m, 2H), 3.48 (s, 3H), 3.55–3.62 (m, 2H), 3.71 (s, 3H), 4.68 (s, 2H), 6.67 (s, 1H), 7.06–7.20 (m, 3H), 7.76 (s, 1H), 8.92 (t, J=7 Hz, 1H).

B. Synthesis of Compound 2

(+)-1,2,3,6-Tetrahydro-1-{N-[4-(2-pyridyl)piperidin-1-yl]propyl}carboxamido-5-methoxycarbonyl-4-methoxymethyl-6-(3,4-difluorophenyl)-2-oxopyrimidine-pyridine-N-oxide hydrochloride a) 4'-tert-Butoxycarbonyl-1',2',3',4',5',6'-hexahydro [2,4']bipyridinyl To a solution of 1',2',3',4',5',6'-hexahydro[2,4']bipyridinyl (1.7 g, 10 mmol) in dichloromethane (100 mL) was added di-tert-butyldicarbonate (2.2 g, 10 mmol) followed by saturated aqueous sodium bicarbonate solution (100 mL). The mixture was stirred vigorously for 2 days, when the layers were separated and the aqueous layer extracted with dichloromethane (1×100 mL). The combined organic layers were dried with sodium sulfate, filtered and concentrated in vacuo to provide crude 4'-tert-butoxycarbonyl-1',2',3',4',5',6'-hexahydro[2,4']bipyridinyl which was used as is in step b.

b) 4'-tert-Butoxycarbonyl-2-oxo-1',2',3',4',5',6'-hexahydro[2,4']bipyridinyl

A solution of 4'-tert-butoxycarbonyl-1',2',3',4',5',6'-hexahydro[2,4']bipyridinyl (10 mmol) in dichloromethane (60 mL) was cooled to 0° C. and was treated with 3-chloroperoxybenzoic acid (4.3 g, 12.5 mmol). The solution was warmed to ambient temperature then stirred 18 h. The reaction was then treated with saturated aqueous sodium bicarbonate solution and the layers separated. The organic layer was dried with magnesium sulfate, filtered and concentrated in vacuo. The crude material was purified by pressurized silica gel chromatography (1–3% methanol in dichloromethane) to afford 4'-tert-butoxycarbonyl-2-oxo-1', 2',3',4',5',6'-hexahydro[2,4']bipyridinyl.

FABMS (M+H)=279 c) 2-oxo-1',2',3',4',5',6'-hexahydro[2,4']bipyridinyl

A solution of 4'-tert-butoxycarbonyl-2-oxo-1',2',3',4',5',6'-hexahydro[2,4']bipyridinyl (2.1 g, 7.6 mmol) in ethyl acetate (150 mL) was cooled to −78° C. Hydrogen chloride gas was bubbled through the solution for 20 min and then the reaction was warmed to ambient temperature. The solid that separated was collected by filtration and dried under vacuum to give the product as a hydrochloride salt. The free base was isolated by standard procedures to provide 2-oxo-1',2',3',4', 5',6'-hexahydro[2,4']bipyridinyl.

d) N-tert-Butoxycarbonyl-3-(3',4',5',6'-tetrahydro-2-oxo-2'H-[2,4']bipyridinyl-1'-yl)propylamine To a solution of 2-oxo-1',2',3',4',5',6'-hexahydro[2,4']-bipyridinyl (0.86 g, 4.8 mmol) in DMF (50 mL) was added 3-bromopropyl-tert-butoxycarbonylamine (1.4 g, 5.8 mmol) and cesium carbonate (1.2 g, 3.6 mmol) under argon. The solution was warmed to 50° C. and stirred 2 days when the reaction was cooled to ambient temperature and the volatiles removed in vacuo. The residue was taken up in dichloromethane (100 mL), washed with saturated sodium carbonate (1×50 mL), dried over magnesium sulfate, filtered, and concentrated in vacuo. The crude material was purified by pressurized silica gel chromatography (1–3% methanol in dichloromethane containing 0.5% NH$_4$OH) to provide N-tert-butoxycarbonyl-3-(3',4',5',6'-tetrahydro-2-oxo-2'H-[2,4']bipyridinyl-1'-yl)propylamine.

FABMS (M+H)=336 e) 3-(3',4',5',6'-Tetrahydro-2-oxo-2'H-[2,4'] bipyridinyl-1'-yl)propylamine dihydrochloride A solution of N-tert-butoxycarbonyl-3-(3',4',5',6'-tetrahydro-2-oxo-2'H-[2,4']bipyridinyl-1'-yl)propylamine (0.63 g, 1.9 mmol) in ethyl acetate (40 mL) was cooled to −78° C. Hydrogen chloride gas was bubbled through the solution for 10 min then the reaction was warmed to ambient temperature. The solid that separated was collected by filtration and dried in vacuo to give the product.

f) (+)-1,2,3,6-Tetrahydro-1-{N-[4-(2-pyridyl) piperidin-1-yl]propyl}carboxamido-5-methoxycarbonyl-4-methoxymethyl-6-(3,4-difluorophenyl)-2-oxopyrimidine-pyridine-N-oxide hydrochloride A solution of (+)-5-methoxycarbonyl-4-methoxymethyl-1,2,3-tetrahydro-2-oxo-6-(3,4-difluorophenyl)-1-[(4- nitrophenyloxy) carbonyl]pyrimidine (200 mg, 0.42 mmol) (as described in Section I.A. (c)) and 3-(3',4',5',6'-Tetrahydro-2-oxo-2'H-[2,4']bipyridinyl-1'-yl)propylamine dihydrochloride (100 mg, 0.42) in THF (20 mL) was stirred at room temperature for 24 hours. Solvent was evaporated and the residue was purified by flash chromatography on silica gel (dichloromethane:MeOH:2M ammonia in MeOH, 980:10:10 to 940:30:30) to give the desired product (252 mg, 98%). MH+574.

C. Synthesis of Compound 3

4-(2-Pyridyl)-1-{3-[5-carboxymethyl-4-methoxymethyl-2-oxo-6(S)-(3,4-difluorphenyl)-1,2,3,6-tetrahydropyrimidin-1-yl]carboxyaminopropyl}pyridinium chloride a) 1-(3-Aminopropyl)-4-(2-pyridyl)pyridinium bromide hydrobromide A solution of 2,4'dipyridyl (820 g, 5.25 mol) and 3-bromopropylamine hydrobromide (1400 g, 6.39 mol) in DMF (5.0 L) was heated to 95° C. for 8 hours. The reaction mixture was cooled to room temperature and methyl tert-butyl ether (3.7 L) was added over 3 hours. The slurry was stirred for 1 hour and filtered. The solid was washed with MTBE/DMF (1:1, 4.2 L) and dried to afford 1-(3-aminopropyl)-4-(2-pyridyl)-pyridinium bromide hydrobromide as a tan solid.

b) 4-(2-Pyridyl)-1-{3-[5-carboxymethyl-4-methoxymethyl-2-oxo-6(S)-(3,4-difluorphenyl)-1,2,3,6-tetrahydropyrimidin-1-yl]carboxyaminopropyl}pyridinium chloride Combined 1-(3-aminopropyl)-4-(2-pyridyl)-pyridinium bromide hydrobromide (227 mg, 0.60 mmol), (+)-5-Methoxycarbonyl-4-methoxymethyl-1,2,3,6-tetrahydro-2-oxo-6-(3,4-difluorophenyl)-1-[(4-nitrophenyloxy)carbonyl]pyrimidine (287 mg, 0.60 mmol) (as described in Section I.A.(c)), and triethylamine (350 mL, 2.51 mmol) in 8 mL of THF and 5 mL of DMF. The yellow mixture was stirred at ambient temperature for 1 hour, then concentrated in vacuo. The resulting oil was purified by a Waters Delta Prep System using a reversed phase C18 cartridge column and a water:acetonitrile gradient containing 0.1% TFA. The product fractions were evaporated to dryness and the resulting residue was treated with HCl/ethyl acetate. The mixture was evaporated to dryness and the residue was reconcentrated from ethyl ether, then triturated with ethyl ether and filtered to give the title compound.

m.p.: 60–85° C. (foam)

NMR: consistent with structure

HPLC: 99% pure

FAB MS: M+H @ m/e=552.2

Anal. cal'd for $C_{28}H_{28}F_2N_5O_5Cl \cdot HCl \cdot 0.80 H_2O$: C, 52.64; H, 4.83; N, 10.96. Found: C, 52.67; H, 4.68; N, 10.77.

D. Synthesis of Compound 4

(+)-4-(2-Pyridyl)-1-{3-[5-carboxymethyl-4-methoxymethyl-2-oxo-6-(3,4-difluorphenyl)-1,2,3,6-tetrahydropyrimidin-1-ylcarbonylamino]propyl}piperidine-1-oxide a) 1-(3-Aminopropyl)-4-[2-pyridyl]pyridinium bromide hydrobromide A solution of 2,4'-dipyridyl (25 g, 160 mmol) and 3-bromopropylamine hydrobromide (35 g, 160 mmol) in DMF (60 mL) was heated at 90–95° C. for 10 h. After cooling to room temperature, anhydrous ether (500 mL) was added to the mixture, the white solid that had formed was filtered, washed with $Et_2O$ and dried to yield 60 g (100%). $^1$H NMR (300 MHZ, DMSO-$d_6$) δ 2.35–2.44 (m, 2H), 3.08–3.13 (m, 2 H), 4.76–4.81 (m, 2 H), 7.58 (dd, J=4.8 Hz, J=7.5 Hz, 1 H), 8.03 (dt, J=1.8 Hz, J=7.8 Hz, 1 H), 8.32 (d, J=7.8 Hz, 1 H), 8.77–8.81 (m, 3 H), 9.12 (d, J=6.3 Hz, 2 H). Anal. Calcd. for $C_{13}H_{16}N_3 \cdot Br \cdot HBr \cdot 0.5 H_2O$: C, 40.65; H, 4.72; N, 10.94. Found: C, 40.83; H, 4.37; N, 11.05.

b) 3-(3',6'-Dihydro-2'-H-[2,4']bipyridinyl-1'-yl)-propylamine

To a solution of 1-(3-aminopropyl)-4-[2-pyridyl]pyridinium bromide hydrobromide (6 g, 16 mmol) in MeOH (150 mL) at 0–5° C. was added $NaBH_4$ (2 g, 53 mmol) in small portions over a period of 2 h. The reaction mixture was stirred overnight at room temperature and the solvent was evaporated. The residue was suspended in ether (200 mL) and treated with 50% NaOH solution (100 mL). The ether layer was separated and the aqueous layer was extracted with more ether (2×50 mL). The combined ether extracts were dried over potassium carbonate and the solvent was removed to give 3-(3',6'-dihydro-2'-H-[2,4']bipyridinyl-1'-yl)-propylamine (3.48 g) as an oil. It was used in the next step immediately without purification.

c) 3-Aminopropyl-4-(2-pyridyl)piperidine

To a solution of 3-(3',6'-dihydro-2'-H-[2,4']bipyridinyl-1'-yl)-propylamine (3.48 g crude, 15.9 mmol) in MeOH (40 mL), was added 1.0 g of Pearlman's catalyst. The suspension was hydrogenated under 120 psi for 10 h after which the reaction mixture was filtered through a pad of Celite and the solvent was removed. The residue was purified by column chromatography over silica gel (30 g) using $CH_2Cl_2$/methanol/2M $NH_3$ in MeOH (90:8:4 to 90:40:40) as eluent. The product was obtained as a pale yellow oil (3.21 g, 91%). $^1$H NMR δ ($CD_3OD$) 1.50–1.99 (m, 10 H), 2.02–2.06 (m, 2 H), 2.37–2.75 (m, 3 H), 3.02–3.06 (br m, 2 H), 7.05–7.09 (m, 4 H), 7.16 (dt, J=0.9 Hz, J=8.7 Hz, 1 H), 8.48 (dd, J=0.9 Hz, J=4.2 Hz, 1 H).

d) (+)-6-(3,4-Difluorophenyl)-1-{N-[4-(2-pyridyl)piperidin-1-yl]propyl]}carboxamido-5-methoxycarbonyl-4-methoxymethyl-2-oxo 1,2,3,6-tetrahydropyrimidine A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (as described in Section I.A.(c)) (2.38 g, 5 mmol), 3-aminopropyl-4-(2-pyridyl)piperidine (1.206 g, 5.5 mmol) in THF (20 mL) was stirred at room temperature for 12 hours. Solvent was evaporated and the residue was redissolved in ethyl acetate (100 mL). It was washed with ice-cold 1N NaOH (4×50 mL), brine (2×50 mL) and dried over potassium carbonate. Solvent was evaporated at reduced pressure and the residue was purified by flash chromatography on silica gel (dichloromethane:MeOH:2M ammonia in MeOH, 980:10:10 to 940:30:30) to give 2.45 g (88%) of very pure product and 0.30 g (10%) of slightly impure fractions, as a foam. $^1$H NMR ($CDCl_3$) δ 1.60–2.00 (m, 6H), 2.05–2.15 (m, 2H), 2.38–2.43 (br t, 2H), 2.65–2.80 (m, 1H), 3.05–3.06 (br d, 2H), 3.30–3.45 (m, 2H), 3.477 (s, 3H), 3.704 (s, 3H), 4.678 (s, 2H), 6.68 (s, 1H), 7.05–7.20 (m, 5H), 7.58–7.63 (dt, 1H), 7.702 (s, 1H, NH), 8.50–8.52 (dd, 1H), 8.875 (br t, 1H).

(e) (+)-4-(2-Pyridyl)-1-{3-[5-carboxymethyl-4-methoxymethyl-2-oxo-6-(3,4-difluorphenyl)-1,2,3,6-tetrahydropyrimidin-1-ylcarbonylamino]propyl}piperidine-1-oxide To a solution of (+)-6(S)-(3,4-difluorophenyl)-1-{3-[4-(2-pyridyl)piperidin-1-yl]propylamino}carbonyl-5-methoxycarbonyl-4-methoxymethyl-2-oxo-1,2,3,6-tetrahydropyrimidine (205 mg, 0.37 mmol) in 4 mL of methanol was added 50% hydrogen peroxide in water (75 mL, 1.30 mmol) and left stir 10 days. The reaction was quenched with the addition of platinum black until oxygen evolution ceased. Filtered the reaction slurry over celite and evaporated the filtrate to dryness to yield a pale yellow oil. The resulting oil was purified by "flash" chromatography (94:6:0.6 of methylene chloride:methanol:ammonium hydroxide). The product fractions were evaporated to dryness, reconcentrated from ethyl ether several times to yield the title product as a yellow foam.

m.p.: 89–115° C. (foam)

NMR: consistent with structure

HPLC: 100% pure

FAB MS: M+H @ m/e=574

Anal. cal'd for $C_{28}H_{33}F_2N_5O_6 \cdot 0.60\ H_2O \cdot 0.10\ Et_2O$: C, 57.63; H, 6.00; N, 11.83. Found: C, 57.64; H, 5.83; N, 11.80.

E. Synthesis of Compound 5

(+)-1,2,3,6-Tetrahydro-1-{N-[4-(2-pyridyl)-4-hydroxypiperidin-1-yl]propyl}carboxamido-5-methoxycarbonyl-4-methoxymethyl-6-(3,4-difluorophenyl)-2-oxopyrimidine dihydrochloride a) N-Benzyl-4-hydroxy-4-(2-pyridyl)piperidine To a stirred solution of 2-bromopyridine (10 mmol) in THF (120 mL) at –78° C. under argon, 2.5 M n-butyl lithium solution in hexane (4.5 mL, 11.25 mmol) was injected over 5 min. After 25 min, 1-benzylpiperidone (10 mmol) was added neat. After 30 min, the mixture was quenched by addition of aqueous $NH_4Cl$ solution (50 mL). The mixture diluted with ethyl acetate (200 mL), washed with brine (150 mL), dried ($Na_2SO_4$). Solvent was evaporated and the residue was purified by column chromatography (silica gel, EtOAc/Hexane from 20% to 60%) to give the desired product(1.78 g, 66.41% ). $^1$H-NMR was consistent with the structure.

b) 4-Hydroxy-4-(2-pyridyl)piperidine

A mixture of N-benzyl-4-hydroxy-4-(2-pyridyl)piperidine (1.2 g, 4.48 mmol), 20% Pd—C (0.2 g) and EtOH (100 mL) was stirred at $H_2$ (150 psi ) for 36 h. The catalyst was removed by filtration and washed with more ethanol. Solvent was evaporated to give pure 4-hydroxy-4-(2-pyridyl)piperidine (0.75 g, 94%).

c) 3-[4-Hydroxy-4-(2-pyridyl)piperidin-1-yl]propylamine

A mixture of 4-hydroxy-4-(2-pyridyl)piperidine (0.730 g, 4.1 mmol), $K_2CO_3$ (0.8 g) and KI (0.1 g) in Acetone (100 mL) and THF (20 mL) was added by N-bromopropylphthalimide (4.5 mmol ) and the mixture was stirred for 14 h. The crude was purified by column chromatography (silica gel, $CH_2Cl_2$:MeOH:2M $NH_3$ in MeOH from 90:4:1 to 75:0:25) to give the product to give the phthalimide-protected side chain (1.376 g, 92%) as a oil. To this, a solution of conc HCl and water (2:1, 25 mL) was added and the mixture was heated for 20 h. Then the reaction mixture was washed and extracted with ether (4×50 mL) to remove the phthalic acid formed. Water was evaporated from the aqueous layer to give a desired product as the HCl salt (1.10 g, 100%). $^1$H-NMR was consistent with the product. This intermediate was treated with 6N NaOH and converted to the free base prior to use in the next step.

d) (+)-1,2,3,6-Tetrahydro-1-{N-[4-(2-pyridyl)-4-hydroxypiperidin-1-yl]propyl}carboxamido-5-methoxycarbonyl-4-methoxymethyl-6-(3,4-difluorophenyl)-2-oxopyrimidine dihydrochloride To a solution of (+)-5-Methoxycarbonyl-4-methoxymethyl-1,2,3,6-tetrahydro-2-oxo-6-(3,4-difluorophenyl)-1-[(4-nitrophenyloxy)carbonyl]pyrimidine (as described in Section I.A.(c)) (201 mg, 0.421 mmol) in dichloromethane (5 mL) was added 3-[4-hydroxy-4-(2-pyridyl)piperidin-1-yl]propylamine (160 mg, 0.729 mmol) at r. t. The resulting mixture was stirred for 2 hours before concentrated to a residue. The residue was purified through column chromatography (chloroform/MeOH/2 N ammonia in MeOH=100:12:6) to afford desired product (212 mg, 88%) . $[\alpha]_D$=+109° C.=0.24 in $CHCl_3$) . The compound was converted to HCl salt by dissolving in 1 N HCl in ether followed by concentrated to dryness. m. p. 135–138° C. Anal. Calcd for $C_{28}H_{33}F_2N_5O_6 \cdot 2HCl$ ($0.4CH_2Cl_2$+$1.0H_2O$): C, 47.61; H, 5.60; N, 9.77. Found: C, 48.39; H, 5.45; N, 9.76. $^1$H-NMR (300 MHZ, $CDCl_3$) δ 1.57–1.68 (m, 2H), 1.75–1.82 (m, 2H), 2.02–2.16(m, 2H), 2.45–2.55 (m, 4H), 2.82–2.86 (m, 2H), 3.35–3.45 (m, 2H), 3.46 (s, 3H), 3.68 (s, 3H), 4.67 (s, 2H), 6.67 (s, 1H), 7.02–7.20 (m, 3H), 7.38 (d, J=8 Hz, 1H), 7.66–7.79 (m, 2H), 8.48–8.50 (d, J=5 Hz, 1H), 8.92(t, J=7Hz, 1H).

F. Synthesis of Compound 6

(+)-2-Oxo-3-{N-[4-(2-pyridyl)piperidin-1-yl]propyl}carboxamido-4-(3,4-difluorophenyl)-5-methoxycarbonyl-6-carboxy-1,2,3,6-tetrahydropyrimidine a) Trimethylsilylethyl oxalate Oxalic acid (13.64 g, 151.4 mmol), trimethylsilyl ethanol (43.4 ml, 303 mmole) and 0.5 ml of concentrated sulfuric acid were combined in 300 ml of benzene and heated to reflux using a Dean-Stark apparatus. After 18 hrs, the reaction mixture was cooled and diluted with 200 ml of ethyl acetate. The reaction mixture was washed with 1N sodium hydroxide solution (2×100 ml), water (1×100 ml) and brine. Rotoevaporation of the dried (magnesium sulfate) organic phase yielded 9 g of the crude product as an oil. Chromatography on silica gel (chloroform elution) afforded 5.61 g of the title compound.

b) Methyl Trimethylsilylethyl oxaloacetate

A solution of 25 ml of tetrahydrofuran containing 1.78 ml (22.38 mmole) of methyl acetate was cooled to –78° C. under nitrogen and treated with 24.6 ml (24.62 mmole) of lithium bis(trimethylsilyl)amide. The reaction mixture was stirred for 1 hr and cannulated into a solution of 25 ml of tetrahydrofuran containing trimethylsilylethyl oxalate at –78° C. After 3.5 hr, the reaction mixture was quenched with water and diluted with 150 ml of ethyl acetate. The organic phase was separated and washed with 1 N hydrochloric acid and brine. Concentration of the dried (magnesium sulfate) extracts yielded and oil which was used without further purification in the next step.

c) Methyl 2-[(3,4-Difluorophenyl)methylene]-trimethylsilylethyl oxaloacetate Methyl trimethylsilylethyl oxaloacetate (4.13 g, 16.78 mmole), 3,4-difluorobenzaldehyde (1.85 ml, 16.78 mmole), piperidine (66 ml, 0.67 mmole), and acetic acid (201 ml, 3.52 mmole) were mixed in 50 ml of benzene at ambient temperature. The reaction mixture was then refluxed for 2.5 hr in a Dean-Stark apparatus. The reaction mixture was cooled, diluted with 100 ml of ethyl acetate, and washed with water and brine. The combined organic extracts were dried with magnesium sulfate and concentrated to give 7 g of a free flowing yellow liquid which was used in the next step without further purification.

d) 2-Methoxy-4-(3,4-difluorophenyl)-5-methoxycarbonyl-6-trimethyl silylethylcarbonyl-1,6-dihydropyrimidine A suspension of 3.7 g (10 mmole) of crude methyl 2-[(3,4-difluorophenyl)methylene]-trimethylsilylethyl oxaloacetate, O-methyl isourea hemisulfate (2.23 g, 13 mmole), and sodium bicarbonate (3.27 g, 39 mmole) in 50 ml of dry N,N-dimethyl formamide was stirred at 55° C. for 6 hr. The reaction mixture was cooled, filtered, and concentrated in vacuo. The residue was dissolved in ethyl acetate and the resulting solution was washed with water. The organic phase was dried (sodium sulfate) and concentrated to afford approximately 3 g of the title compound in crude form. This material was used in the next step without further purification.

e) 4-(3,4-Difluorophenyl)-5-methoxycarbonyl-6-trimethylsilylethyl carbonyl-1,2,3,6-tetrahydropyrimidin-2-one 2-Methoxy-4-(3,4-difluorophenyl)-5-methoxycarbonyl-6-trimethylsilylethyl carbonyl-1,6-dihydropyrimidine (3 g, 7 mmole) in crude form was dissolved in 20 ml of tetrahydrofuran and treated with 2 ml of 12 N hydrochloric acid. The resulting reaction mixture was stirred at ambient temperature for 2.5 hr. The pH of the reaction mixture was adjusted to 7 with 2 N lithium hydroxide solution and the reaction mixture was concentrated in vacuo to leave the aqueous phase. The aqueous layer was extracted with ethyl acetate. The combined organic extracts were washed with brine, dried (magnesium sulfate), and concentrated. The crude product was purified employing preparative centrifugal thin layer chromatography (hexane-ethyl acetate elution) to yield 900 mg of the title compound. $^1$H NMR (CDCl$_3$) d 0.06 (s, 9H), 1.07 (m, 2H), 3.63 (s, 3H), 4.36 (m, 2H), 5.38 (d, 1H) 5.73 (br. s, 1H), 7.02–7.2 (m, 3H), 7.52 (br. s, 1H).

f) 2-Oxo-3-[(4-nitrophenyloxy)carbonyl]-4-(3,4-difluorophenyl)-5-methoxycarbonyl-6-trimethylsilylethylcarbonyl-1,2,3,6-tetrahydro pyrimidine To a solution of 4-(3,4-difluorophenyl)-5-methoxycarbonyl-6-trimethylsilyl ethylcarbonyl-1,2,3,6-tetrahydropyrimidin-2-one (478 mg, 1.16 mmole) in 25 ml of dry tetrahydrofuran at −78° C. under nitrogen was added 0.7 ml (1.39 mmole) of lithium diisopropylamide. After addition was complete, the reaction mixture was stirred for 1 hr and cannulated into a solution of 15 ml of tetrahydrofuran containing 280 mg (1.39 mmole) of 4-nitrophenyl chloroformate). The reaction was stirred for 1 hr more, warmed to room temperature and partitioned between 100 ml of ethyl acetate and 50 ml of 1N sodium carbonate solution. The organic phase was washed once more with sodium carbonate and then with brine. The combined organic extracts were dried (sodium sulfate) and concentrated to give a yellow semi-solid. The crude product was flash chromatographed on silica gel (chloroform-acetone elution, 9:1, v/v) to give the title compound as a pale yellow solid.

g) (±)-2-Oxo-3-{N-[4-(2-pyridyl)piperidin-1-yl]propyl}carboxamido-4-(3,4-difluorophenyl)-5-methoxycarbonyl-6-trimethylsilylethylcarbonyl-1,2,3,6-tetrahydropyrimidine 3-Aminopropyl-4-(2-pyridyl)piperidine (240 mg, 1.1 mmole) was combined with 2-oxo-3-[(4-nitrophenyloxy)carbonyl]-4-(3,4-difluorophenyl)-5-methoxycarbonyl-6-trimethylsilylethylcarbonyl-1,2,3,6-tetrahydro pyrimidine (577 mg, 1.1 mmole) in 10 ml of dry tetrahydrofuran at ambient temperature. The resulting solution was stirred for 2 hr and then diluted with 50 ml of ethyl acetate. The reaction mixture was then washed in succession with 1N hydrochloric acid, 10% sodium carbonate solution, 1N, hydrochloric acid, and brine. The combined organic extracts were dried (sodium sulfate) and concentrated to give 550 mg of crude product. This material was purified via preparative centrifugal thin layer chromatography on silica gel (chloroform-methanol elution) to yield 228 mg of the title compound. $^1$H NMR (CDCl$_3$) d 0.06 (s, 9H), 1.07 (m, 2H), 1.78 (m, 2H), 1.91 (m, 4H), 2.1 (m, 2H), 2.45 (m, 2H), 2.71 (m 1H), 3.05 (m, 2H), 3.31 (ddd, 1H), 3.42 (ddd, 1H), 3.72 (s, 3H), 4.32 (m, 2H), 6.60 (s, 1H) 7.05–7.35 (m, 6H), 7.61 (ddd, 1H), 8.51 (d, 1H), 8.87 (dd, 1H).

h) (+)-2-Oxo-3-{N-[4-(2-pyridyl)piperidin-1-yl]propyl}carboxamido-4-(3,4-difluorophenyl)-5-methoxycarbonyl-6-trimethylsilylethylcarbonyl-1,2,3,6-tetrahydropyrimidine Racemic 2-oxo-3-{N-[4-(2-pyridyl)piperidin-1-yl]propyl}carboxamido-4-(3,4-difluorophenyl)-5-methoxycarbonyl-6-trimethylsilylethylcarbonyl-1,2,3,6-tetrahydro pyrimidine was resolved by chiral HPLC [Chiralpak AD, 250×20 mm; l 315 nm; isocratic conditions 80% hexanes:20% 2-propanol containing 0.2% diethylamine; flow rate=6.0 ml/min]. The first of the two enantiomers to elute was collected to give 110 mg of the title compound. Analytical chiral chromatography [Chiralpak AD, 250×4.6 mm, 1 280 nm; isocratic conditions 80% hexanes-20% 2-propanol containing 0.1% diethylamine; flow rate=2.0 ml/min] showed the title compound to be 98.66% pure.

i) (+)-2-Oxo-3-{N-[4-(2-pyridyl)piperidin-1-yl]propyl}carboxamido-4-(3,4-difluorophenyl)-5-methoxycarbonyl-6-carboxy-1,2,3,6-tetrahydropyrimidine (+)-2-Oxo-3-{N-[4-(2-pyridyl)piperidin-1-yl]propyl}carboxamido-4-(3,4-di fluorophenyl)-5-methoxycarbonyl-6-trimethylsilylethylcarbonyl-1,2,3,6-tetrahydropyrimidine (110 mg, 0.16 mmole) was dissolved in 2 ml of dry tetrahydrofuran and treated with 33 mL (0.33 mmole) of 1M tetrabutyl ammonium fluoride solution in tetrahydrofuran. The reaction mixture was protected from moisture and heated to 60° for 2 hr. All volatiles were removed under reduced pressure and the residual material was purified by preparative thin layer chromatography (ethyl acetate-pyridine-acetic acid-water elution, 90:10:1:1, v/v) to give the title compound as an off-white solid. HPLC: 95.5%.

¹H NMR (DMSO-d₆) d 1.7–1.9 (m, 8H), 2.78 (m, 2H), 3.2–3.4 (m, 5H), 3.54 (s, 3H), 6.41 (s, 1H), 7.10 (m, 1H), 7.2 (m, 3H), 7.29 (d, 1H), 7.41 (dd, 1H), 7.71 (dd, 1H), 8.49 (d, 1H), 8.89 (dd, 1H), 9.91 (br. s, 1H). FAB MS: 558 (M⁺+H), 580 (M⁺+Na).

G. Synthesis of Compound 7

(+)-1,2,3,6-Tetrahydro-1-{N-[4-(2-pyridyl)piperidin-1-yl]propyl}carboxamido-5-methoxycarbonyl-4-hydroxymethyl-6-(3,4-difluorophenyl)-2-oxopyrimidine a)(+)-1,2,3,6-Tetrahydro-1-{N-[4-(2-pyridyl)piperidin-1-yl]propyl}carboxamido-5-methoxycarbonyl-4-hydroxymethyl-6-(3,4-difluorophenyl)-2-oxopyrimidine To a solution of (+)-1,2,3,6-tetrahydro-1-{N-[4-(2-pyridyl)piperidin-1-yl]propyl}carboxamido-5-methoxycarbonyl-4-methoxymethyl-6-(3,4-difluorophenyl)-2-oxopyrimidine (250 mg, 0.448 mmol) (as described in Section I.D. (d) in dichloromethane (20 mL) at −78° C. was added boron tribromide (1.0 M in dichloromethane, 1.20 mL, 1.20 mmol) dropwise: The cooling bath was removed and the reaction mixture was stirred while warmed gradually to r. t. for 4 hours before quenched with MeOH (5 mL) and concentrated to a residue. The residue was purified through preparative thinlayer chromatography using chloroform/MeOH/2 N ammonia in MeOH= 100:4:1 as the eluent to afford desired product (15 mg, 6%). MS: (M+H) 544. ¹H-NMR (300 MHZ, CDCl₃) δ 1.79–1.98 (m, 6H), 2.05–2.12 (m, 2H), 2.45(t, J=7 Hz, 2H), 2.68–2.76 (m, 1H), 3.04–3.08 (m, 2H), 3.25–3.42 (m, 2H), 3.68 (s, 3H), 4.95 (dd, J=17 Hz, 23 Hz, 2H), 6.65 (s, 1H), 6.97–7.23 (m, 5H), 7.62 (t, J=8 Hz, 1H), 8.48–8.50 (d, J=5 Hz, 1H), 8.98(t, J=7 Hz, 1H).

H. Synthesis of Compound 8

(+)-1-3-{[4-(3,4-Difluorophenyl)-2,5-dioxo-1,2,5,7-tetrahydro-4H-furo[3,4-d]-pyrimidine-3-carbonyl]amino}-propyl-4-(2-pyridyl)-piperidine a) Methyl 2-{(3,4-difluorophenyl)methylene}-3-oxobutyrate A mixture of 3,4-difluorobenzaldehyde (14.2 g, 0.1 mol), methyl acetoacetate (12.2 g, 0.105 mol), piperidine (0.430 g, 5 mmol), and acetic acid (0.30 g, 5 mmol) in benzene (150 mL) was stirred and refluxed with a Dean-Stark trap for 8 hours. Benzene was evaporated, the residue was dissolved in ethyl acetate (200 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2-{(3,4-difluorophenyl)methylene}-3-oxobutyrate, was obtained as a yellow oil (0.98 g, 98.3%) and was used in the next step without any further characterization.

b) 6-(3,4-Difluorophenyl)-1,6-dihydro-2-methoxy-5-methoxycarbonyl-4-methylpyrimidine A mixture of methyl 2-{(3,4-difluorophenyl)methylene}-3-oxobutyrate (8.8 g, 36.6 mmol), O-methylisourea hydrogen sulfate (9.4 g, 55 mmol), and NaHCO₃ (12.3 g, 0.146 mol) in DMF (30 mL) was stirred and heated at 70° C. for 16 hours. The mixture was cooled, diluted with EtOAc (300 mL) and washed with water (5×300 mL), brine (300 mL), and dried (MgSO₄). Solvent was evaporated and the crude product was purified by flash column chromatography on silica gel using 10% through 20% EtOAc in hexane as the gradient eluent, to leave the product as an oil (3.82 g, 30.2%); ¹H-NMR (CDCl₃): δ 2.32,2.39 (2 s, 3 H), 3.58, 3.64 (2 s, 3 H), 3.72, 3.85 (2 s, 3 H), 5.55 ( s, 1H), 6.13–7.8 (m, 4 H).

c) 6-(3,4-Difluorophenyl)-1,6-dihydro-2-methoxy-5-methoxycarbonyl-4-methyl-1-[(4-nitrophenyloxy)-carbonyl]pyrimidine To a solution of 6-(3,4-diifluorophenyl)1,6-dihydro-2-methoxy-5-methoxycarbonyl-4-methylpyrimidine (2.82 g, 9.52 mmol) and 4-dimethylaminopyridine (1.16 g, 9.52 mmol) in CH₂Cl₂ (50 mL), at 0–5° C., 4-nitrophenyl chloroformate (1.82 g, 9.04 mmol) was added and the mixture was allowed to warm to room temperature. After 12 hours solvent was evaporated and the residue was purified by flash column chromatography (SiO₂, EtOAc/hexane, 10–15%) to obtain the product as white crystals (3.72, 84.7%); m.p. 172–174° C.; ¹H-NMR (CDCl₃): δ 2.51 (s, 3 H), 3.72(s, 3 H), 3.97 (s, 3 H), 6.26 (s, 1H), 7.0–7.3 (m, 3 H), 7.38 (d, J=9.3 Hz, 2 H), 8.32 (d J=9.3 Hz, 2 H).

d) (+)-6-(3,4-Difluorophenyl)-1,6-dihydro-2-oxo-5-methoxy-carbonyl-4-bromomethyl-1-[(4-nitrophenyl-oxy)carbonyl]pyrimidine To a well stirred solution of (+)-6-(3,4-difluorophenyl)-1,6-dihydro-2-methoxy-5-methoxycarbonyl-4-methyl-1-[(4-nitrophenyloxy)carbonyl]pyrimidine (1.5 mmol, 0.66 g) in 5 mL of chloroform was added a solution of bromine (1.5 mmol, 0.09 mL) in 3 mL of chloroform at 0° C. and the solution was allowed to attain room temperature over 1.5 h. The solvent was removed in vacuo and the residue was again dissolved in CHCl₃ (20 mL) and washed with brine. The organic layer was separated, dried over Na₂SO₄, filtered and the solvent was removed in vacuo to get 0.81 g of (+)-6-(3,4-difluorophenyl)-1,6-dihydro-2-oxo-5-methoxycarbonyl-4-bromomethyl-1-[(4-nitrophenyloxy)carbonyl]pyrimidine as a yellow foam. It was used in the next step without any purification. ¹H NMR δ 3.75 (s, 3 H), 4.67 (ABq, d$_A$=4.56, d$_B$=4.78, J=10.8 Hz, 2 H), 6.35 (s, 1 H), 7.09–7.19 (m, 4 H) 7.37 (d, J=9.0 Hz, 2 H), 8.27 (d, J=9.0 Hz, 2 H).

e) (+)-4-(3,4-Difluoro-phenyl)-2,5-dioxo-1,2,4,5,6,7-hexahydro-cyclopetapyrimidine-3-carboxylic acid-4-nitrophenyl ester (+)-6-(3,4-Difluorophenyl)-1,6-dihydro-2-oxo-5-methoxy-carbonyl-4-bromomethyl-1-[(4-nitrophenyloxy)carbonyl]pyrimidine (1.5 mmol, 0.81 g) was heated in oil bath for 3 h (bath temperature 130° C.). The brown residue thus obtained was washed with CHCl₃ and (+)-4-(3,4-difluoro-phenyl)-2,5-dioxo-1,2,4,5,6,7-hexahydro-cyclopenta pyrimidine-3-carboxylic acid-4-nitrophenyl ester was obtained as a pale brown solid which was used in the next step without further purification (crude wt. 0.51 g). ¹H NMR (DMSO) δ 4.94 (br,s, 2 H), 6.08 (s, 1 H), 7.20–7.43 (m, 4 H), 8.35 (d, J=10.2 Hz, 2 H).

f) (+)-1-3-{[4-(3,4-Difluorophenyl)-2,5-dioxo-1,2,5,7-tetrahydro-4H-furo[3,4-d]-pyrimidine-3-carbonyl]amino}-propyl-4-(2-pyridyl)-piperidine A solution of (+)-4-(3,4-difluoro-phenyl)-2,5-dioxo-1,2,4,5,6,7-hexahydro-cyclopenta pyrimidine-3-carboxylic acid-4-nitrophenyl ester ((0.33 mmol, 0.14 g) and 3-[4-(2-pyridyl)-piperidin-1-yl)propyl amine (0.33 mmol, 0.07 g) in 10 mL of anhydrous THF was stirred overnight at room temperature. The solvent was removed in vacuo and the residue was purified by column chromatography ($CH_2Cl_2$ followed by 9:1 $CH_2Cl_2$/MeOH) to obtain (+)-1-3-{[4-(3,4-difluorophenyl)-2,5-dioxo-1,2,5,7-tetrahydro-4H-furo[3,4-d]-pyrimidine-3-carbonyl]amino}-propyl-4-(2-pyridyl)-piperidine as an oil. (0.16 g, 98%). $^1$H NMR δ 1.77–1.98 (m, 6 H), 2.20–2.25 (m, 2 H), 2.54 (t, J=7.2 Hz, 2 H), 2.74–2.80 (m, 1 H), 3.11–3.18 (m, 2 H), 3.29–3.39 (m, 2 H), 4.86 (s, 2 H), 6.04 (br s, 1 H), 6.46 (s, 1 H), 7.07–7.26 (m, 5 H), 7.63 (dt, J=7.8 Hz, J=1.8 Hz, 1 H), 8.48 (d, J=3.9 Hz), 9.22 (br t, J=5.1 Hz, 1 H). It was characterized as a dihydrochloride salt (hygroscopic). M.P. 90–95° C.; [α]=+43.4 (c=0.25, acetone); Anal. Calcd. For $C_{26}H_{29}N_5O_4F_2Cl_2 \cdot 4.0\ H_2O$: C, 47.57; H, 5.68; N, 10.67. Found: C, 47.59; H, 5.32; N, 10.79.

I. Synthesis of Compound 9

3-(3-Carboxypropylcarbamoyl)-4(S)-(3,4-difluorophenyl)-2-oxo-1,2,3,4-tetrahydro-4H-furo[3,4-d]pyrimidine a) (+)5-Methoxycarbonyl-4-methoxymethyl-1,2,3,6-tetrahydro-2-oxo-6(S)-(3,4-difluorophenyl)-1-[(2-ethoxycarbonylethylamino)-carbonyl]pyrimidine β-Alanine ethyl ester hydrochloride (87 mg, 0.57 mmol), (+)-5-methyoxycarbonyl-4-methoxymethyl-1,2,3,6-tetrahydro-2-oxo-6(S)-(3,4-difluorophenyl)-1-[(4-nitrophenyloxy)-carbonyl]pyrimidine (as described in Section I.A.(c)) (227 mg, 0.48 mmol), and triethylamine (209 mL, 1.50 mmol) were combined in 5 mL of dichloromethane. The yellow mixture was stirred at ambient temperature for 1 hour, then evaporated to dryness. The resulting oil was purified by "flash" chromatography (5.02, 98:2:0.2 of dichloromethane:methanol:ammonium hydroxide). The product fractions were evaporated to dryness to give the title compound as a clear oil.

b) (+)-5-Methoxycarbonyl-4-methoxymethyl-1,2,3,6-tetrahydro-2-oxo-6(S)-(3,4-difluorophenyl)-1-[(2-carboxyethylamino)-carbonyl]pyrimidine (+)-5-Methoxycarbonyl-4-methyoxymethyl-1,2,3,6-tetrahydro-2-oxo-6(S)-(3,4-difluorophenyl)-1-[(2-ethoxycarbonylethylamino)carbonyl]pyrimidine (168 mg, 0.37 mmol) was dissolved in 5 mL of methanol. A 2.0M solution of aqueous sodium hydroxide (400 mL, 0.80 mmol) was added dropwise. The mixture was stirred at ambient temperature for 4.5 hours, then concentrated in vacuo. The resulting residue was partioned between ethyl acetate and 2.0M aqueous hydrochloric acid. The phases were separated and the aqueous phase was extracted twice with ethyl acetate. The combined organic phases were then washed with brine. The organic phase was then dried over sodium sulfate, filtered, and the filtrate was then evaporated to dryness. The residue was reconcentrated from diethyl ether. The resulting white foamy solid was purified by "flash" chromatography (5.02, 98:2:0.2 of dichloromethane:methanol:glacial acetic acid). The product fractions were evaporated to dryness and the residue was reconcentrated from diethyl ether to give the title compound as a white foamy solid.

m.p.: 52–55° C.
NMR: consistent with structure
HPLC: 100% pure
FAB MS: M+H @ m/e=428.0

Anal. cal'd for $C_{18}H_{19}F_2N_3O_7 \cdot 0.15H_2O \cdot 0.10Et_2O$: C, 50.51; H, 4.68; N, 9.61. Found: C, 50.50; H, 4.46; N, 9.51.

c) 3-(2-Carboxyethylcarbamoyl)-4(S)-(3,4-difluorophenyl)-2,5-dioxo-1,2,3,4-tetrahydro-4H-furo[3,4-d]pyrimidine (+)-5-Methoxycarbonyl-4-methoxymethyl-1,2,3,6-tetrahydro-2-oxo-6(S)-(3,4-difluorophenyl)-1-[(2-carboxyethylamino)carbonyl]pyrimidine(308 mg, 0.72 mmol) was dissolved in 5 mL of dichloromethane, and then cooled to −78° C. in a dry ice/acetone bath while stirring under a nitrogen atmosphere. A 1.0M solution of boron tribromide in dichloromethane (3.25 mL, 3.3 mmol) was then added. The mixture was stirred at −78° C. for 45 minutes, then slowly warmed to ambient temperature over 1 hour. 15 mL of sat'd sodium bicarbonate was added until a neutral pH was achieved. The mixture was stirred at ambient temperature for 10 minutes. Volatile components were removed by evaporation. The resulting aqueous solution was stirred at ambient temperature for 18 hours. Aqueous solution was then acidified with concentrated hydrochloric acid, precipitating a white solid which was filtered. The resulting white solid was purified by preparative reverse phase HPLC using an $H_2O$: $CH_3CN$ gradient containing 0.1% TFA. The product fractions were evaporated to dryness to give the title compound as a white solid.

NMR: consistent with structure
HPLC: 96.2% pure
FAB MS: M+H @ m/e=382.1

II. Synthesis of Other Possible Precursors

Schemes 4A and 4B describe the synthesis of other possible precursors which may be utilized to prepare additional compounds (Marquis, et al. *J. Med. Chem.* (1998) 41: 3563).

III. Oral Composition

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Profiles of the Compounds in Cloned Human Adrenergic Receptors Binding affinities were measured for selected compounds of the invention at six cloned human $α_1$ and $α_2$ receptor subtypes, as well as at the L-type calcium channel. The protocols for these experiments are given below.

1. Protocol for the Determination of the Potency of $α_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$α_{1d}$ Human Adrenergic Receptor: The entire coding region of $α_{1d}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the $\alpha_{1a}$ receptor gene (old nomenclature)) and the plasmid pGCcos3neo (plasmid containing the aminoglycoside transferase gene) into LM(tk–) cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

The cell line expressing the human $\alpha_{1d}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1d}$ receptor, was accorded ATCC Accession No. CRL 11138, and was deposited on Sep. 25, 1992.

$\alpha_{1b}$ Human Adrenergic Receptor: The entire coding region of $\alpha_{1b}$ (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above. The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CR 11139, on Sep. 29, 1992.

$\alpha_{1a}$ Human Adrenergic Receptor: The entire coding region of $\alpha_{1a}$ (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. The stable cell line expressing the human $\alpha_{1a}$ receptor used herein was designated L-$\alpha_{1C}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1a}$ receptor was accorded Accession No. CR 11140, on Sep. 25, 1992.

Radioligand Binding Assays for $\alpha_1$ receptors: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 MM $MgCl_2$, and 0.1% ascorbic acid at pH 7.5. Binding of the $\alpha_1$ antagonist [$^3$H]prazosin (0.5 nM, specific activity 76.2 Ci/mmol) to membrane preparations of LM(tk–) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors: To determine the potency of $\alpha_1$ antagonists at the $\alpha_2$ receptors, LM(tk–) cell lines stably transfected with the genes encoding the $\alpha_{2a}$, $\alpha_{2b}$, and $\alpha_{2c}$ receptors were used. The cell line expressing the $\alpha_{2a}$ receptor is designated L-$\alpha_{2A}$, and was deposited on Nov. 6, 1992 under ATCC Accession No. CRL 11180. The cell line expressing the $\alpha_{2b}$ receptor is designated L-NGC-$\alpha_{2B}$, and was deposited on Oct. 25, 1989 under ATCC Accession No. CRL10275. The cell line expressing the $\alpha_{2c}$ receptor is designated L-$\alpha_{2C}$, and was deposited on Nov. 6, 1992 under ATCC Accession No. CRL-11181. All the cell lines were deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10 μM phentolamine. The bound radioligand was separated by filtration through GF/B filters using a cell harvester.

Determination of the Activity of $\alpha_1$ Antagonists at Calcium Channels

The potency of $\alpha_1$ antagonists at calcium channels may be determined in competition binding assays of [3H] nitrendipine to membrane fragments of rat cardiac muscle, essentially as described by Glossman and Ferry (Methods in Enzymology 109:513–550, 1985). Briefly, the tissue is minced and homogenized in 50 mM Tris-HCl (pH 7.4) containing 0.1 mM phenylmethylsulfonyl fluoride. The homogenates are centrifuged at 1000 g for 15 minutes, and the resulting supernatant centrifuged at 45,000 g for 15 minutes. The 45,000 g pellet is suspended in buffer and centrifuged a second time. Aliquots of membrane protein are then incubated for 30 minutes at 37° C. in the presence of [3H]nitrendipine (1 nM), and nonspecific binding determined in the presence of 10 μM nifedipine. The bound radioligand is separated by filtration through GF/B filters using a cell harvester.

The compounds described above were assayed using cloned human alpha adrenergic receptors. The preferred compounds were found to be selective $\alpha_{1a}$ antagonists.

The binding affinities of several compounds are illustrated in the following table.

Binding affinities of selected compounds of the present invention at cloned human $\alpha_{1d}$, $\alpha_{1b}$, $\alpha_{1a}$, $\alpha_{2a}$, $\alpha_{2b}$, and $\alpha_{2c}$ receptors (h=human).

| Compound | $h\alpha_{1a}$ | $h\alpha_b$ | $h\alpha_{1d}$ | $h\alpha_{2a}$ | $h\alpha_{2b}$ | $h\alpha_{2c}$ |
|---|---|---|---|---|---|---|
| 1 | 260 | >50,000 | >50,000 | 40,000 | 26,000 | >50,000 |
| 2 | 0.3 | 1,500 | 3,700 | 4,200 | 8,700 | 1,500 |
| 3 | 212 | >2,000 | >5,000 | 5,623 | 9,661 | 3,388 |
| 4 | 2.1 | 1,354 | >5,000 | 22,000 | 17,000 | 8,000 |
| 6 | 23.5 | >2,000 | >5,000 | >50,000 | 37,584 | >50,000 |
| 7 | 0.8 | 530 | 1200 | 380 | 1200 | 260 |
| 8 | 3 | 1,600 | 1,970 | 1,500 | 970 | 1,500 |
| 9 | >500 | >2,000 | >5,000 | >50,000 | >50,000 | >50,000 |
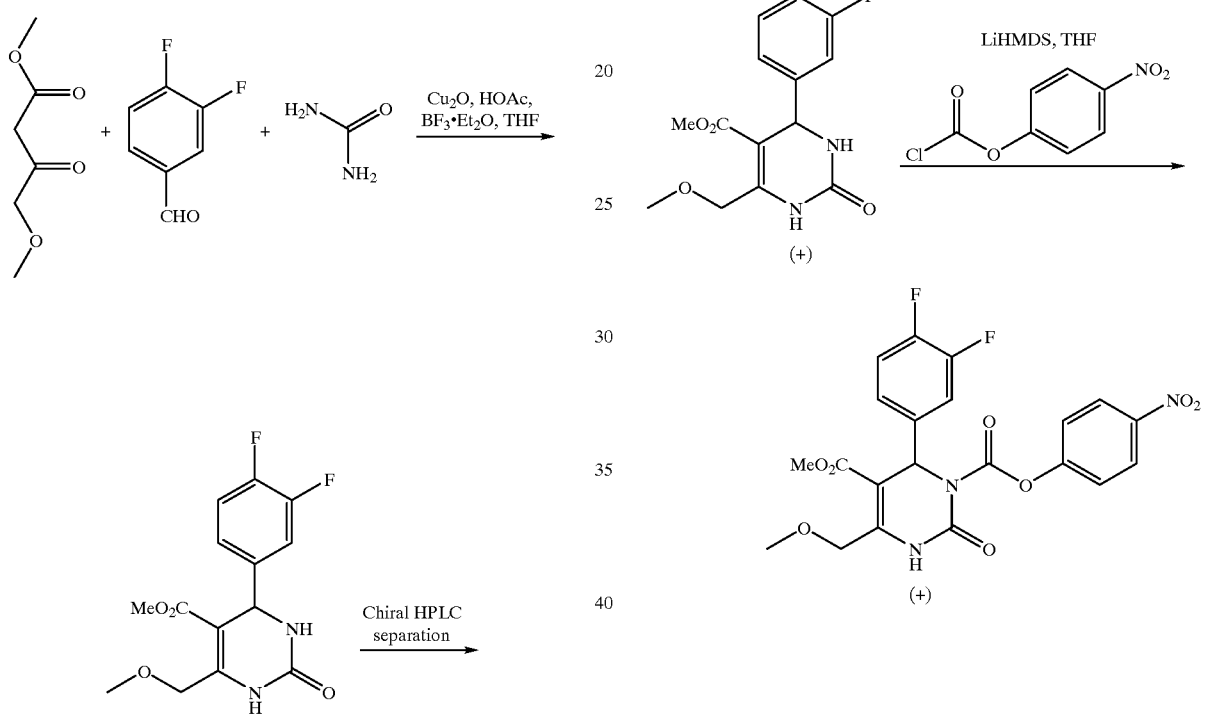
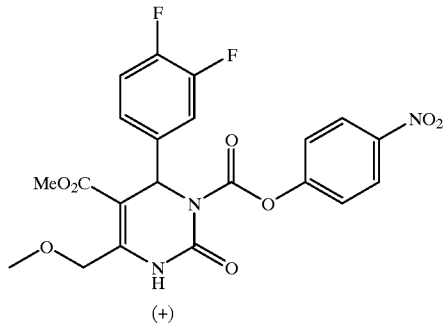
Scheme 2: Synthesis of compounds

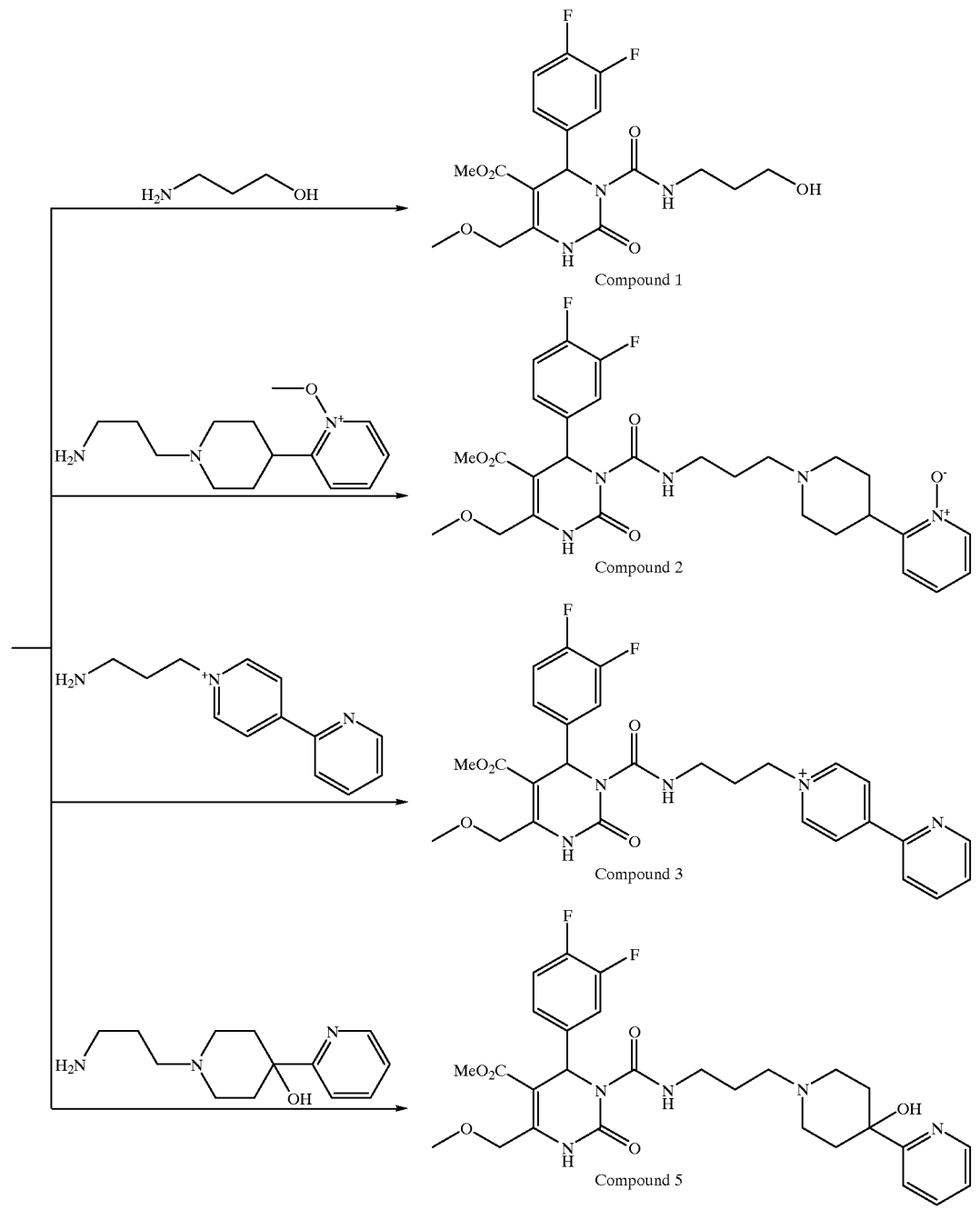
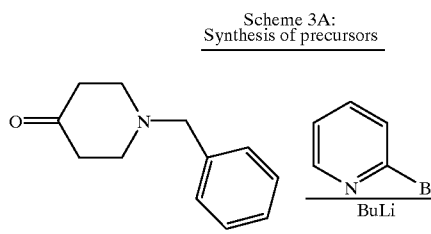
Scheme 3A:
Synthesis of precursors
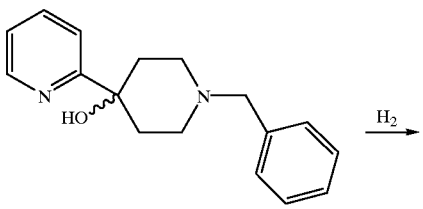
-continued

31
-continued
1.
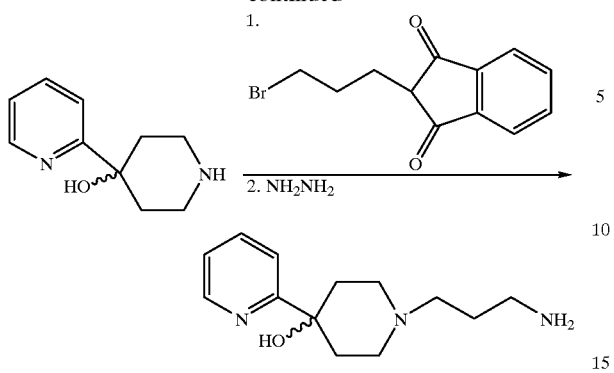
2. NH₂NH₂
32
-continued
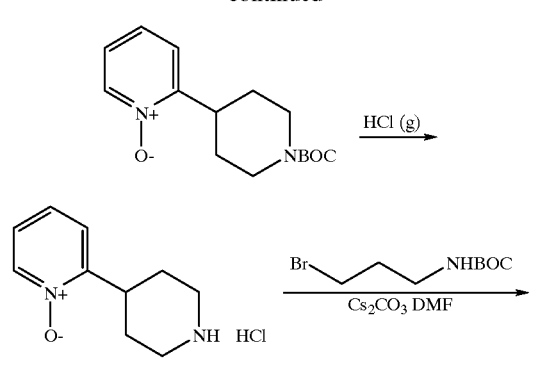
Scheme 3B:
Synthesis of precursors
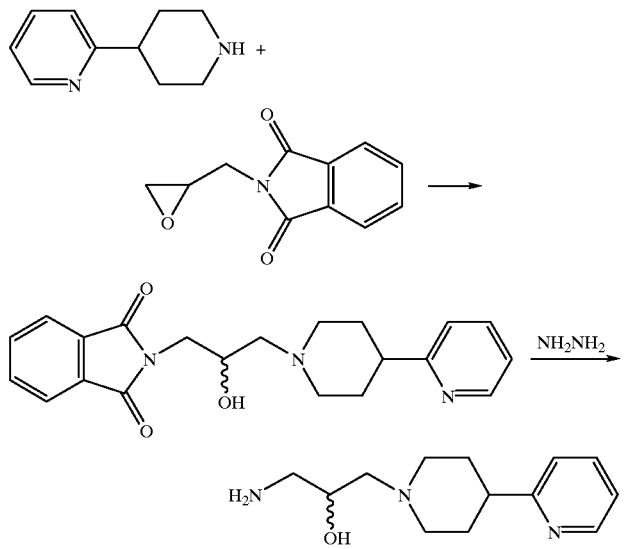
NH₂NH₂
Scheme 3C:
Synthesis of precursors
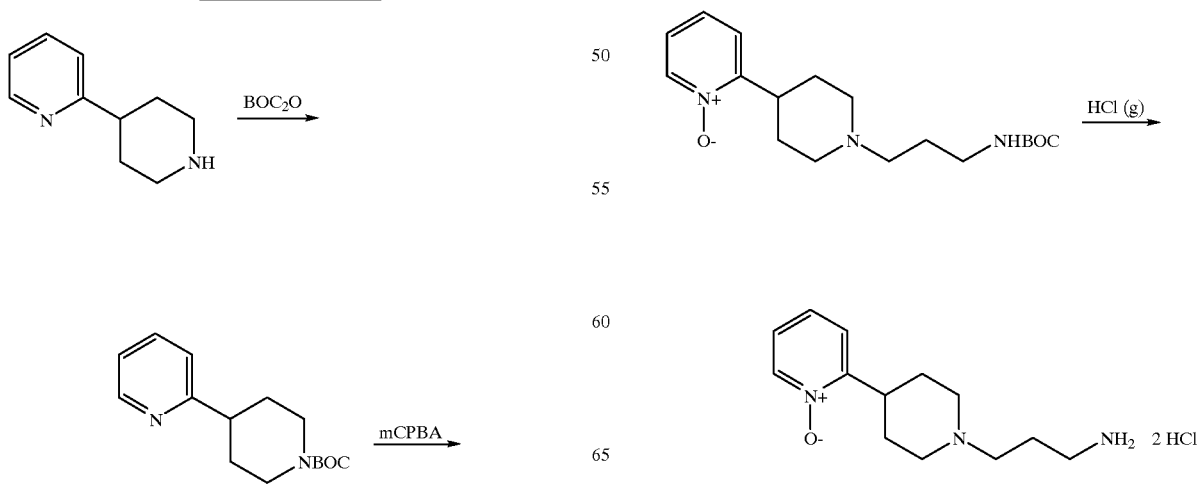

Scheme 4A:
Possible Synthetic schemes for precursors
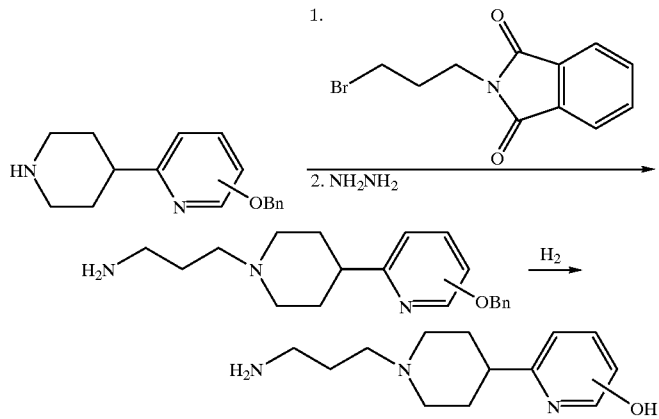
Scheme 4B:
Possible Synthetic schemes for precursors
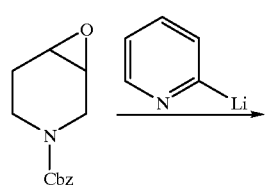
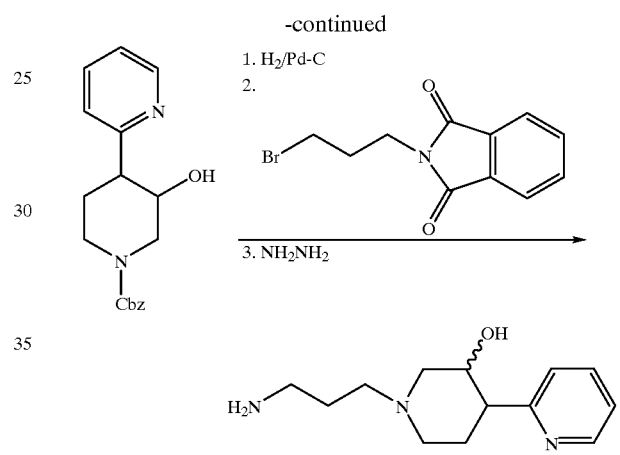
Scheme 5:
Synthesis of Compound 6
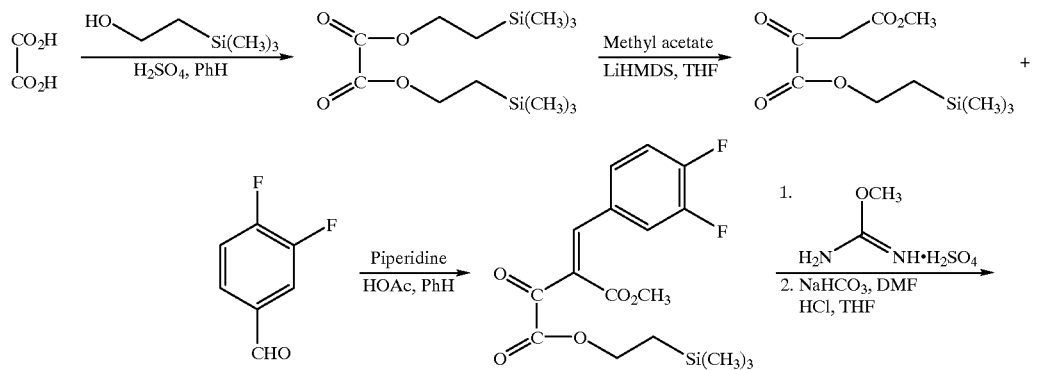

-continued
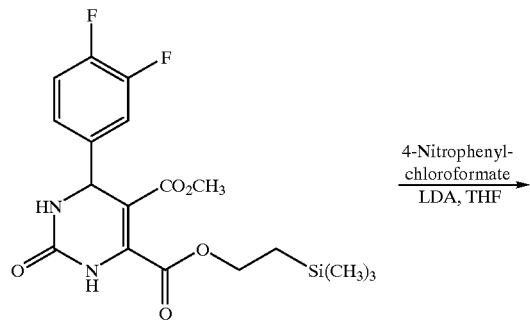
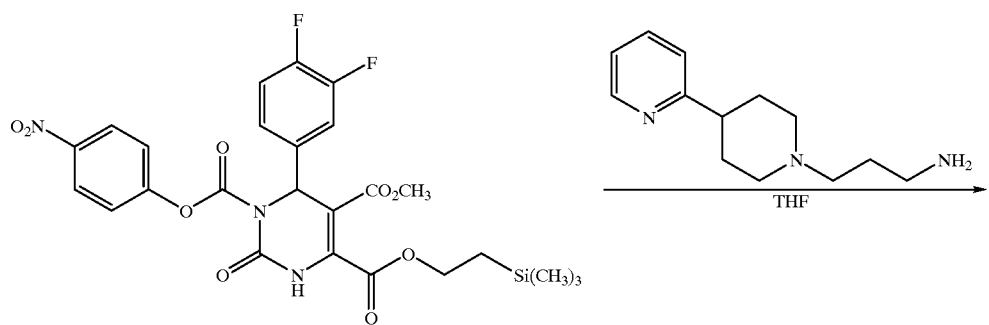
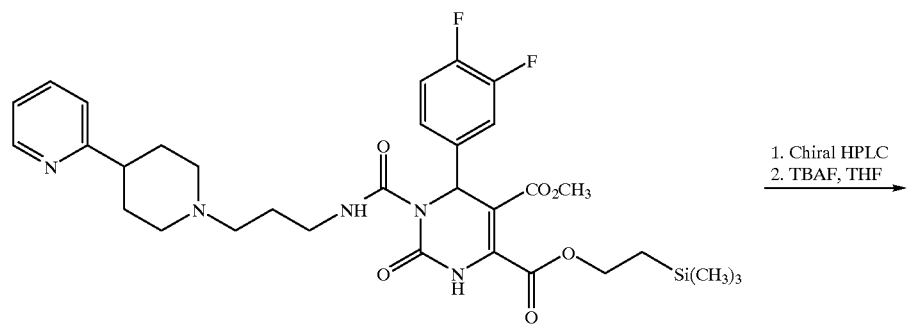
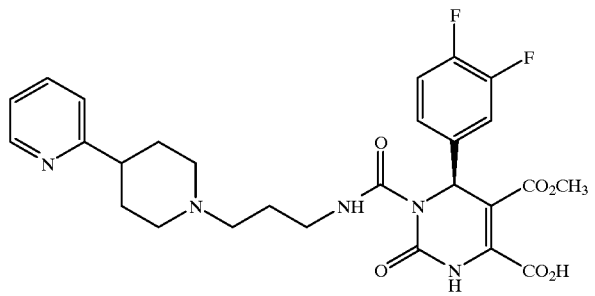

Scheme 6
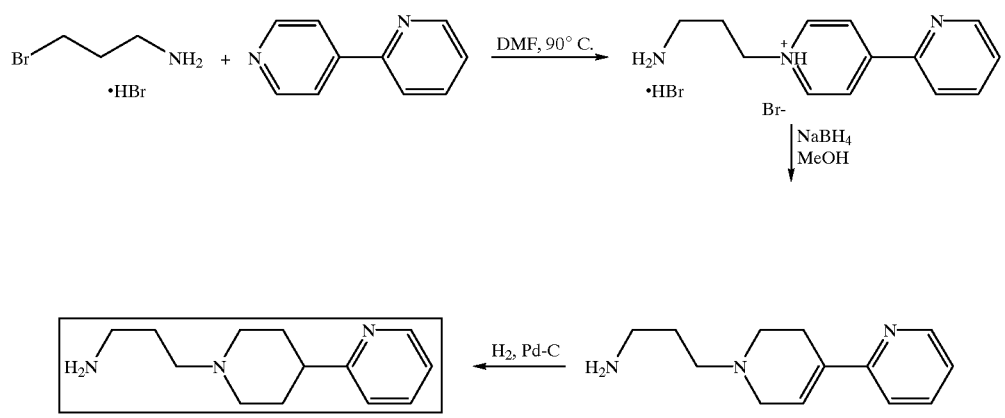
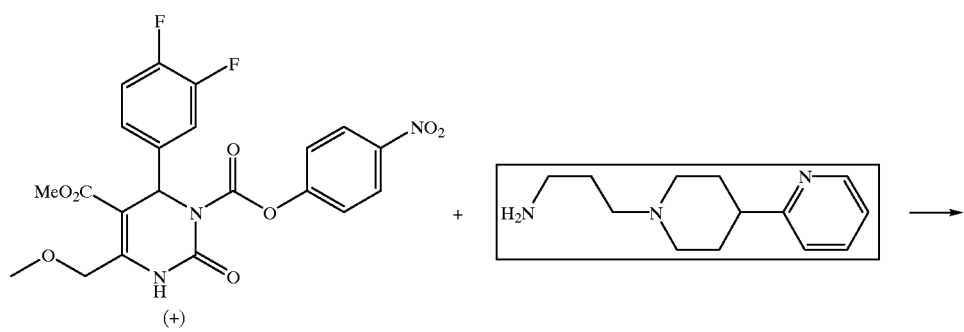
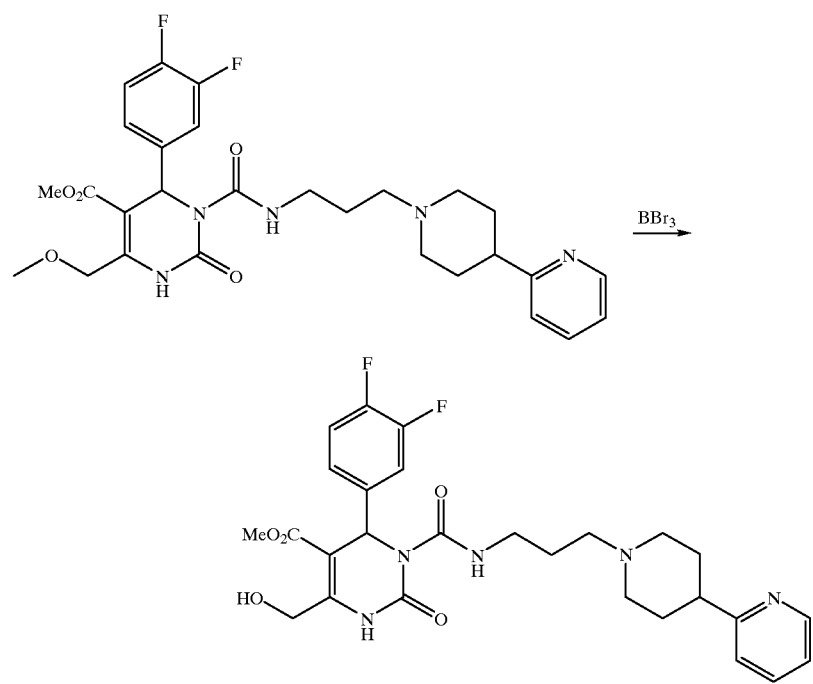

Scheme 7: Synthesis of Compound 8
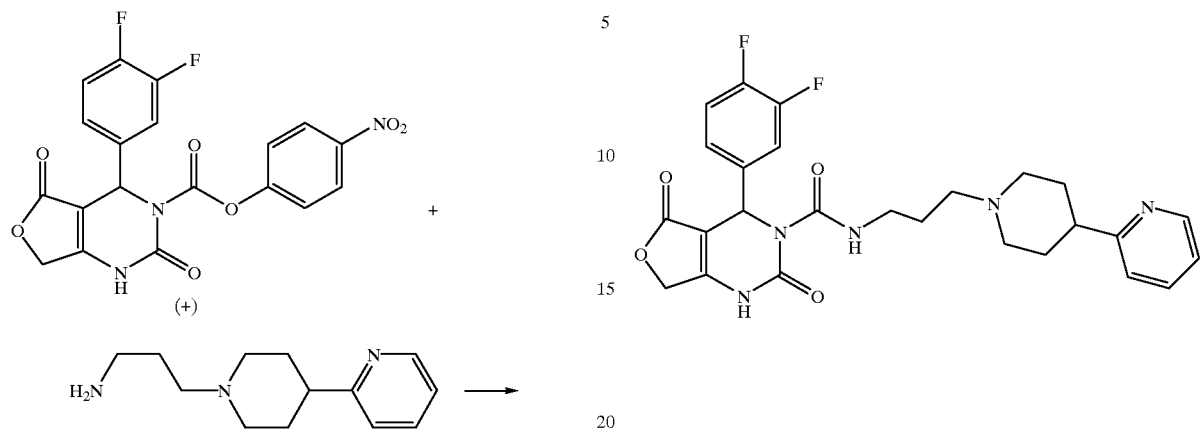
Scheme 8: Synthesis of Compound 9
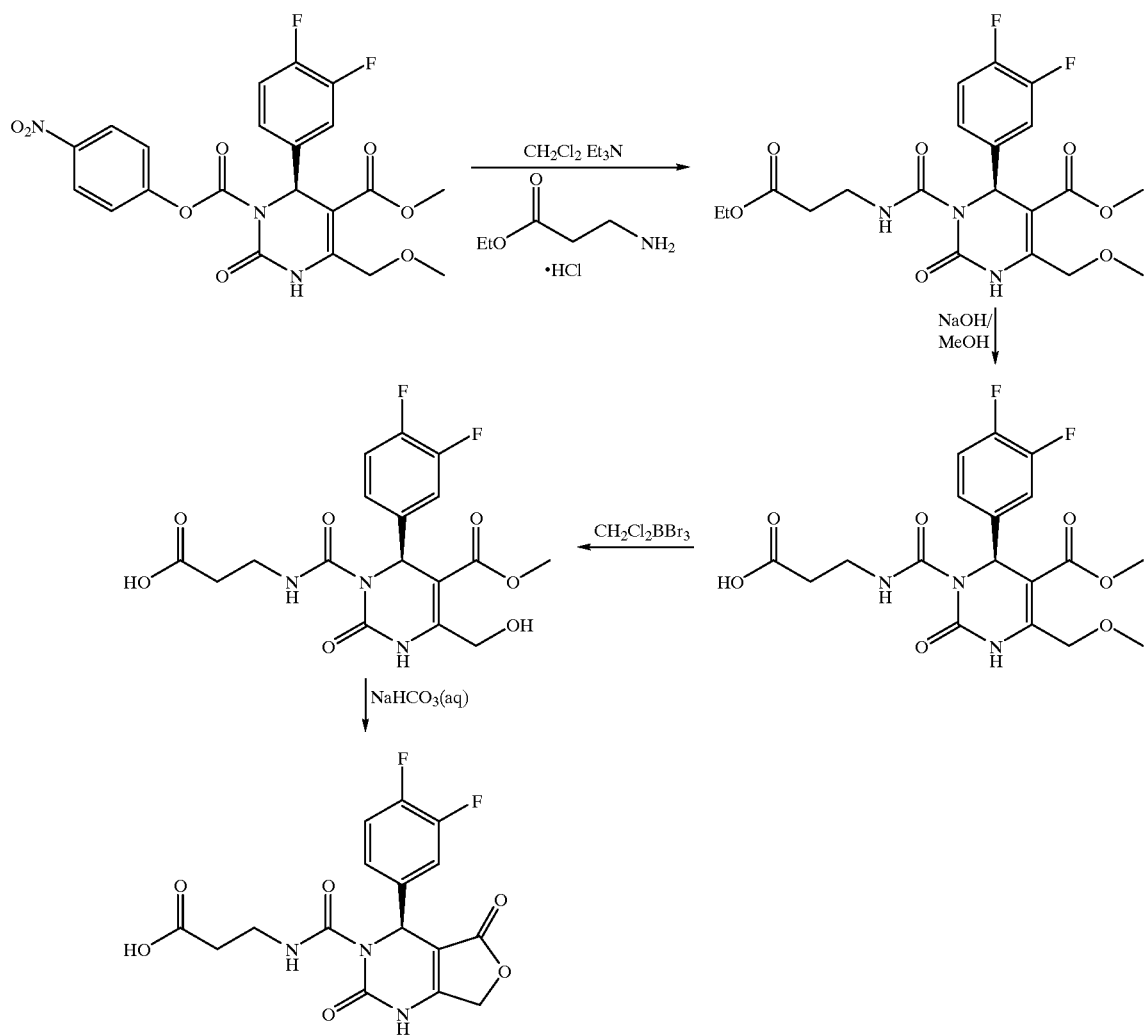
Compound 9

What is claimed is:

1. A compound having the structure:

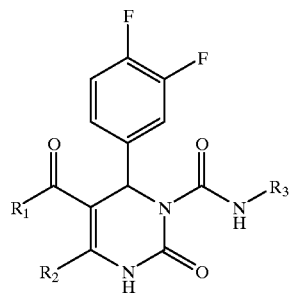

wherein $R_1$ is —$OCH_3$ or OH;
wherein $R_2$ is —$CH_2OH$, —$CH_2OCH_3$, or —COOH; or
wherein $R_1$ and $R_2$ together form a 5-membered lactone ring;
wherein $R_3$ is selected from the group consisting of —$(CH_2)_3OH$,

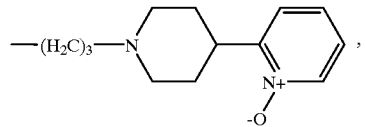

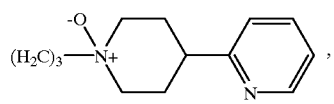

and

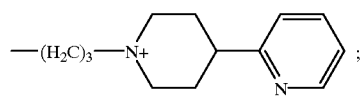

or a pharmaceutically acceptable salt thereof.

2. The (−) enantiomer of the compound of claim 1.
3. The (+) enantiomer of the compound of claim 1.
4. The compound of claim 3 having the structure:

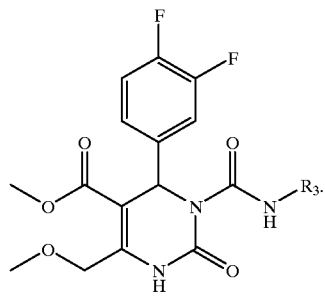

5. The compound of claim 4 having the structure:

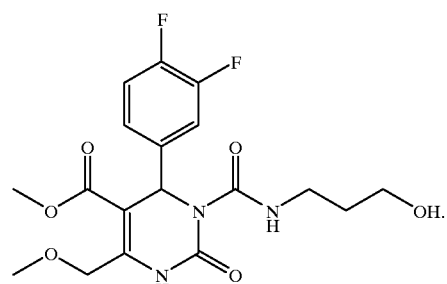

6. The compound of claim 4 having the structure:

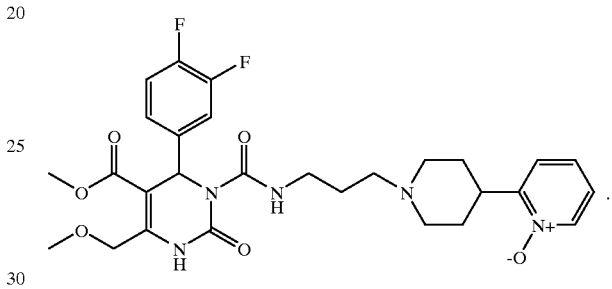

7. The compound of claim 4 having the structure:

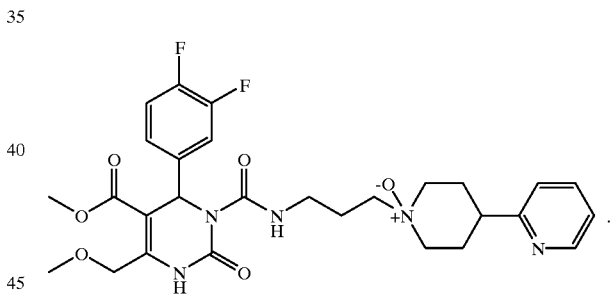

8. A pharmaceutically acceptable salt comprising a compound having the structure:

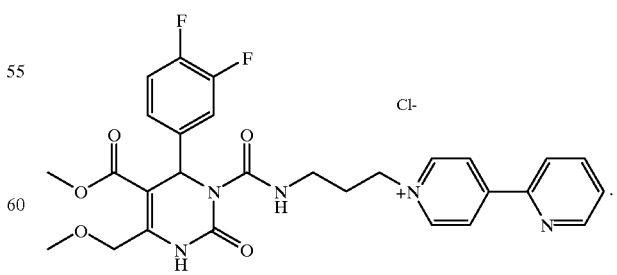

9. A compound having the structure:

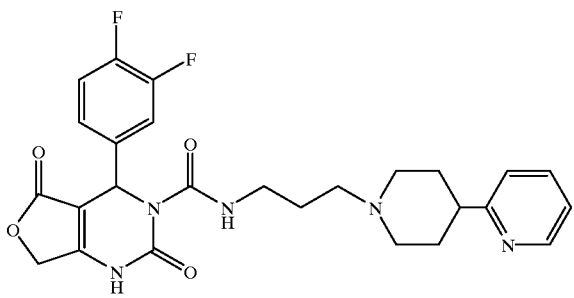

or a pharmaceutically acceptable salt thereof.

10. A compound having the structure:

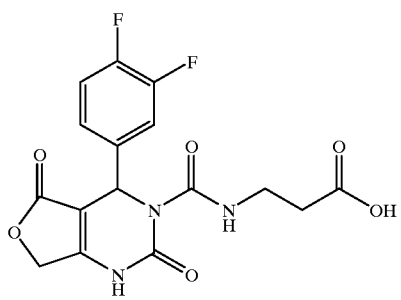

or a pharmaceutically acceptable salt thereof.

11. A pharmaceutical composition comprising a therapeutically effective amount of the compound of claim 1 or 9 and a pharmaceutically acceptable carrier.

12. The pharmaceutical composition of claim 11, wherein the therapeutically effective amount is an amount from about 0.01 mg to about 500 mg.

13. The pharmaceutical composition of claim 12, wherein the therapeutically effective amount is an amount from about 0.1 mg to about 60 mg.

14. The pharmaceutical composition of claim 13, wherein the therapeutically effective amount is an amount from about 1 mg to about 30 mg.

15. The pharmaceutical composition of claim 11, wherein the carrier is a liquid and the composition is a solution.

16. The pharmaceutical composition of claim 11, wherein the carrier is a solid and the composition is a tablet.

17. The pharmaceutical composition of claim 11, wherein the carrier is a gel and the composition is a suppository.

18. A pharmaceutical composition comprising a therapeutically effective amount of the compound of claim 1 or 9 in combination with therapeutically effective amount of finasteride and a pharmaceutically acceptable carrier.

19. The pharmaceutical composition of claim 18, wherein the therapeutically effective amount of the compound is an amount from about 0.01 mg to about 500 mg and the therapeutically effective amount of the finasteride is about 5 mg.

20. The pharmaceutical composition of claim 18, wherein the therapeutically effective amount of the compound is an amount from about 0.1 mg to about 60 mg and the therapeutically effective amount of the finasteride is about 5 mg.

21. The pharmaceutical composition of claim 18, wherein the therapeutically effective amount of the compound is an amount from about 1 mg to about 30 mg and the therapeutically effective amount of the finasteride is about 5 mg.

22. A process for making a pharmaceutical composition which comprises combining a therapeutically effective amount of a compound of claim 1 or 9 and a pharmaceutically acceptable carrier.

23. A method of treating a subject suffering from benign prostatic hyperplasia which comprises administering to the subject an amount of the compound of claim 1 or 9 effective to treat benign prostatic hyperplasia.

24. A method of treating a subject suffering from benign prostatic hyperplasia which comprises administering to the subject an amount of the compound of claim 1 or 9 in combination with a 5 alpha-reductase inhibitor effective to treat benign prostatic hyperplasia.

25. The method of claim 24, wherein the 5-alpha reductase inhibitor is finasteride.

26. A method of relaxing lower urinary tract tissue which comprises administering to the subject an amount of the compound of claim 1 effective to relax lower urinary tract tissue.

27. The method of claim 26, wherein the lower urinary tract tissue is urethral smooth muscle.

28. A method of inhibiting contraction of prostatic tissue in a subject which comprises administering an amount of a compound according to claim 1 or 9 effective to inhibit contraction of prostatic tissue.

29. A method of treating a disease which is susceptible to treatment by antagonism of the $\alpha_{1A}$ receptor which comprises administering to the subject an amount of the compound of claim 1 or 9 effective to treat the disease.

* * * * *

UNITED STATES PATENT AND TRADEMARK OFFICE
CERTIFICATE OF CORRECTION

PATENT NO. : 6,274,585 B1
DATED : August 14, 2001
INVENTOR(S) : Donghui Cui et al.

It is certified that error appears in the above-identified patent and that said Letters Patent is hereby corrected as shown below:

Column 41,
Lines 19-20, "COOH; or wherein" should read -- COOH; wherein --
Lines 31-35, that portion of the formula reading Lines 41-45, that portion of the formula reading

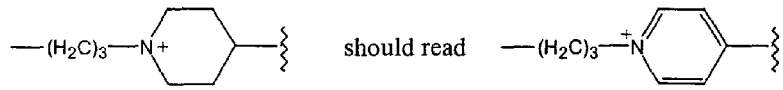

Line 51, "claim 3" should read -- claim 1 --

Column 43,
Line 34, "claim 1 or 9" should read -- claim 1, 6, or 9 --

Signed and Sealed this

Eighteenth Day of March, 2003

JAMES E. ROGAN
*Director of the United States Patent and Trademark Office*